United States Patent [19]
Muhlhauser et al.

[11] Patent Number: 5,712,271
[45] Date of Patent: Jan. 27, 1998

[54] METHOD OF TREATING URINARY BLADDER DYSFUNCTIONS

[76] Inventors: Mark A. Muhlhauser, 4811 Basil Ct., Indianapolis, Ind. 46237; Harlan E. Shannon, 4229 Rolling Springs Dr., Carmel, Ind. 46234; Karl B. Thor, 4959 Jennings Dr., Carmel, Ind. 46033

[21] Appl. No.: 725,523

[22] Filed: Oct. 3, 1996

Related U.S. Application Data

[62] Division of Ser. No. 336,357, Nov. 8, 1994, Pat. No. 5,612,351.

[51] Int. Cl.$^6$ .......... A61K 31/44; A61K 31/55; A61K 31/41; A61K 31/415

[52] U.S. Cl. .......... 514/212; 514/213; 514/304; 514/305; 514/342; 514/362; 514/364; 514/381; 514/397; 514/406; 514/415; 514/438; 514/444; 514/468; 514/649; 514/650

[58] Field of Search .......... 514/212, 213, 514/304, 305, 342, 362, 364, 381, 397, 406, 415, 444, 438, 468, 648, 650

[56] References Cited

U.S. PATENT DOCUMENTS

| | | | |
|---|---|---|---|
| 5,041,455 | 8/1991 | Sauerberg et al. | 514/342 |
| 5,043,345 | 8/1991 | Sauerberg et al. | 514/342 |
| 5,260,314 | 11/1993 | Sauerberg et al. | 514/305 |
| 5,418,240 | 5/1995 | Sauerberg et al. | 514/305 |

FOREIGN PATENT DOCUMENTS

| | | |
|---|---|---|
| 0 239 309 | 9/1987 | European Pat. Off. . |
| 0 244 018 | 11/1987 | European Pat. Off. . |
| 0 296 721 | 12/1988 | European Pat. Off. . |
| 0 301 729 | 2/1989 | European Pat. Off. . |
| 0 307 142 | 3/1989 | European Pat. Off. . |
| 0 316 718 | 5/1989 | European Pat. Off. . |
| 0 322 182 | 6/1989 | European Pat. Off. . |
| 0 328 200 | 8/1989 | European Pat. Off. . |
| 0 349 956 | 1/1990 | European Pat. Off. . |
| 0 384 285 | 8/1990 | European Pat. Off. . |
| 0 459 568 | 12/1991 | European Pat. Off. . |

*Primary Examiner*—Theodore J. Criares
*Attorney, Agent, or Firm*—Steve T. Zelson; Elias J. Lambiris

[57] ABSTRACT

The present invention relates to a novel method for treating a mammal suffering from urinary bladder dysfunctions.

8 Claims, No Drawings

METHOD OF TREATING URINARY BLADDER DYSFUNCTIONS

This is a divisional application of application Ser. No. 08/336,357, filed Nov. 8, 1994 now U.S. Pat. No. 5,612,351, the contents of which are incorporated herein by reference in their entirety.

BACKGROUND OF THE INVENTION

The present invention provides a novel method using cholinergic agonists for treatment of sensory abnormalities of the bladder such as urge incontinence, urinary frequency, urgency, nocturia and interstitial cystitis, or contractile dysfunction.

The function of the lower urinary tract is storage and periodic release of urine. Inability to store urine is called urinary incontinence. There are two clinically-recognized forms of incontinence, stress incontinence and urge incontinence. Stress incontinence is defined as a loss of urine which results from urethral sphincter insufficiency during periods of elevated abdominal pressure (i.e. stress), while urge incontinence is due to bladder smooth muscle hyperactivity which is accompanied by feelings of urgency to urinate. Bladder hyperactivity, without loss of urine, can also lead to urinary frequency, urgency, and nocturia, which are also clinically significant problems for a large patient population. Urgency may also be accompanied by pelvic pain, which arises from the bladder. This condition is termed interstitial cystitis. Bladder hyperreflexia, urgency, and interstitial cystitis are dependent upon the sensory innervation of the bladder, particularly those sensations which are perceived as noxious.

Currently prescribed medicines, which include muscarinic cholinergic antagonists (i.e. anti-cholinergics such as oxybutynin) or spasmolytics (such as flavoxate), suppress bladder contractions by effecting the efferent or motor component of micturition, but which have no effect or exacerbate the sensory components of bladder dysfunction. By suppressing the ability of the bladder to contract, these compounds prevent the bladder from completely emptying and thus produce significant residual urine, which is conducive to the formation of bladder infection. Furthermore, since these drugs do not effect the sensory limb of bladder function, they are not effective for conditions such as interstitial cystitis. Often, these latter patients must resort to removal of the bladder for treatment of their bladder pain. Thus, we believe that a drug that suppresses the ability of the bladder to contract and reduces noxious sensory input from the bladder would be useful for treating bladder dysfunctions.

We have discovered a new class of muscarinic agents which have not previously been considered for treating urinary bladder dysfunctions.

SUMMARY OF THE INVENTION

The method of this invention comprises administering to a patient suffering from urinary bladder dysfunction an effective amount of a compound of the formula I

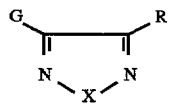

wherein

X is oxygen or sulphur;

R is hydrogen, amino, halogen, —CHO, —$NO_2$, —$R^4$, —Y, —NHCO—$R^4$, —$OR^4$, —$SR^4$, —$SOR^4$, —$SO_2R^4$, $C_{3-10}$-cycloalkyl, $C_{4-10}$-cycloalkenyl, $C_{4-10}$-(cycloalkylalkyl) —$Z^1$—$C_{3-10}$-cycloalkyl, —$Z^1$—$C_{4-10}$-cycloalkenyl, —$Z^1$—$C_{4-10}$-(cycloalkylalkyl), —Z—$C_{4-10}$-(cycloalkenylalkyl), —$Z^1$—$C_{4-10}$-(methylenecycloalkylalkyl), —NH—$R^4$, —$NR^4R^5$, —NH—$OR^4$, —CH=$NOR^4$, phenyl, benzyloxycarbonyl, phenoxy, benzoyl, tetrahydronaphthyl, naphtyl, indenyl, wherein each aromatic group is optionally substituted with halogen, —$NO_2$, —CN, $C_{4-10}$-alkyl, $C_{4-10}$-alkoxy, —$OCF_3$, —$CONH_2$, —$CSNH_2$, phenoxy or phenyl; or R is —$Z^1$—$R^6$—$Z^2$—$R^5$, —$Z^1$—$R^6$—$Z^2$—$R^7$—$Z^3$—$R^5$, —$Z^1$—CO—$R^5$, —$Z^1$—$R^6$—CO—$R^5$, —$Z^1$—$R^6$—$CO_2$—$R^5$, —$Z^1$—$R^6$—$O_2C$—$R^5$, —$Z^1$—$R^6$—CONH—$R^5$, —$Z^1$—$R^6$—NHCO—$R^5$, —Z—$R^6$—Y, —$Z^1$—$R^6$—$Z^2$—Y, wherein $Z^1$ and $Z^2$ independently are oxygen or sulphur, and $R^4$ and $R^5$ independently are straight or branched $C_{1-15}$-alkyl, straight or branched $C_{2-15}$-alkenyl, straight or branched $C_{2-15}$-alkynyl, each of which is optionally substituted with one or more halogen(s), $C_{1-6}$-alkoxy, —$CF_3$, —CN, —COOH, —OH, —$NH_2$, $C_{1-6}$-alkyl ester, —SH, —$NHR^4$, —$NR^4R^5$, phenyl or phenoxy, wherein each aromatic group is optionally substituted with halogen, —$NO_2$, —CN, $C_{1-4}$-alkyl, $C_{1-4}$-alkoxy, —$OCF_3$, —$CONH_2$, —$CSNH_2$, phenyl or phenoxy, and wherein $R^6$ and $R^7$ independently are straight or branched $C_{1-10}$-alkylene, straight or branched $C_{2-10}$-alkenylene, straight or branched $C_{2-10}$-alkynylene, each of which is optionally substituted with one or more halogen(s), —$CF_3$, —CN, —COOH, —OH, —$NH_2$, $C_{1-6}$-alkyl ester, —SH, —$NHR^4$, —$NR^4R^5$, phenyl or phenoxy, and Y is a 5 or 6 membered heterocyclic group containing one to four N, O or S atom(s) or a combination thereof, which heterocyclic group is optionally substituted at carbon or nitrogen atom(s) with straight or branched $C_{1-6}$-alkyl, phenyl or benzyl, or a carbon atom in the heterocyclic group together with an oxygen atom form a carbonyl group, or which heterocyclic group is optionally fused with a phenyl group; and G is selected from one of the following azabicyclic rings

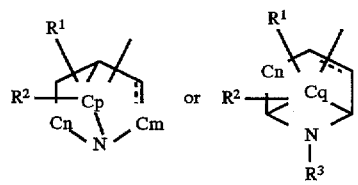

wherein the thiadiazole or oxadiazole ring can be attached at any carbon atom of the azabicyclic ring; $R^1$ and $R^2$ may be present at any position, including the point of attachment of the thiadiazole or oxadiazole ring, and independently are hydrogen, straight or branched $C_{1-5}$-alkyl, straight or branched $C_{2-5}$-alkenyl, straight or branched $C_{2-5}$-alkynyl, straight or branched $C_{1-10}$-alkoxy, straight or branched $C_{1-5}$-alkyl substituted with —OH, —OH, halogen, —$NH_2$ or carboxy; $R^3$ is H, straight or branched $C_{1-5}$-alkyl, straight or branched $C_{2-5}$-alkenyl or straight or branched $C_{2-5}$-alkynyl; n is 0, 1 or 2; m is 0, 1 or 2; p is 0, 1 or 2; q is 1 or 2; and ⋯ is a single or double bond; or a pharmaceutically acceptable salt thereof.

Examples of such salts include inorganic and organic acid addition salts such as hydrochloride; hydrobromide, sulphate, phosphate, acetate, fumarate, maleate, citrate, lactate, tartrate, oxalate, or similar pharmaceutically acceptable inorganic or organic acid addition salts, and include the pharmaceutically acceptable salts listed in Journal of Pharmaceutical Science, 66, 2 (1977) which are hereby incorporated by reference.

Especially preferred salts include tartrate and hydrochloride.

As used herein, the term "patient" includes any mammal which could benefit from treatment of urinary bladder dysfunctions. The term particularly refers to a human patient, but is not intended to be so limited.

The thiadiazole and oxadiazole compounds used in the presently claimed method have been disclosed and claimed in PCT/DK91/00236. The thiadiazole and oxadiazole derivatives are known to be cholinergic muscarinic agents useful in the treatment of presenile and senile dementia. The compounds are believed to be useful for treating Alzheimer's disease, glaucoma, and painful conditions. Other disclosures suggest that thiadiazole compounds may be useful for the treatment of illnesses whose clinical manifestations are due to cholinergic deficiency, (European Patent Application 307142). Such illnesses include Huntington's chorea, tardive dyskinesia, hyperkinesia, mania, and Tourette Syndrome.

The compounds of this method produce a dose-dependent inhibition of vesico-anal reflex activity that is reversed by atropine, a centrally active muscarinic antagonist.

In addition, the compounds of this method have been found to have a favourable profile of activity in a number of in vitro binding assays, designed to measure the degree of binding to neural receptors.

The compounds have $IC_{50}$ levels of less than 1 µM in the $^3$H-oxotremorine-M binding assay, indicating that the compounds have muscarinic receptor affinity.

This profile of activity in in vitro receptor binding assays, like that observed in the acetic acid-induced vesico-anal reflex test, would indicate that the compounds are effective in the treatment of urinary bladder dysfunctions.

Methods

The model of visceral nociception that was used in the testing of the compounds according to the method of this invention is the acetic acid-induced vesico-anal reflex. This model utilizes infusion of a dilute acetic acid solution into the urinary bladder as a nociceptive stimulus and records increases in electromyographic (EMG) activity from the anal sphincter as the primary measured response. Anal sphincter EMG activity is composed of 2 components, 1) a small, long duration action potential (ca. 50 msec) that is sensitive to muscarinic antagonists and 2) a larger, short duration action potential (ca. 2 msec) that is sensitive to neuromuscular blocking agents (i.e. mediated by nicotinic receptors). These components represent rectal longitudinal smooth muscle activity and external anal sphincter striated muscle activity, respectively, and have been described in detail in a separate publication (Muhlhauser reference). It is the striated anal sphincter muscle activity that 1) is associated with bladder activity, 2) is increased by acetic acid infusion into the bladder, and 3) represents the vesico-anal reflex. The acetic acid-induced increase in vesico-anal reflex activity is maintained for over 2 hours in 95% of the animals.

In the acetic acid-induced vesico-anal reflex model, bladders of urethane-anesthetized rats were cannulated through the dome for continuous-infusion cystometrogram recordings. EMG electrodes were inserted into the anus and the peri-urethral musculature for recording anal and urethral sphincteric activity, respectively. Infusion of 0.5% acetic acid into the bladder or urethra produced modest increases in bladder contractile activity and urethral sphincter activity and pronounced increases in anal sphincter activity (i.e. an increase in the vesico-anal reflex). Oxotremorine (1–30 µg/kg iv), a centrally-active cholinergic agonist, and the test compounds (0.01–1.0 mg/kg iv) produced dose-dependent inhibition of vesico-anal reflex activity (to 10% of control) that was reversed by atropine (0.3–1 mg/kg), a centrally active muscarinic antagonist. Scopolamine methyl bromide (1–30 ug/kg), a peripherally-restricted muscarinic antagonist, was ineffective at blocking the cholinergic agonist-mediated inhibition of the vesico-anal reflex. This indicates that oxotremorine-induced inhibition of the VA reflex and that of the test compounds was centrally mediated. Furthermore, when atropine (30 µg/kg–1 mg/kg) and oxybutynin (1–3 mg/kg, a muscarinic antagonist used clinically for bladder dysfunction) were administered alone, robust, but transient (15 min.), increases in vesico-anal reflex activity were recorded. This indicated that endogenous acetylcholine was partially suppressing the vesico-anal reflex via tonic muscarinic mechanisms. This indication was supported by the finding that the centrally active cholinesterase inhibitor, physostigmine (but not the peripherally-restricted cholinesterase inhibitor, neostigmine) also suppressed the VA reflex in a dose-dependent, atropine-sensitive manner. These studies indicate that a tonically-active, endogenous, cholinergic muscarinic system plays a role in the suppression of visceral nociception arising from the lower urinary tract.

Experimental

Female Sprague-Dawley rats (200–300 g) were anesthetized with 1.4 g/kg urethane (0.7 g administered i.p. and 0.7 g administered s.c.), which was supplemented with 1% isoflurane during surgery. The urinary bladder was exposed through an abdominal incision and cannulated with PE60 tubing attached to a 22 gauge needle that was inserted through the dome of the bladder. A purse-string suture (5-0 silk) through the bladder held the needle in place. The cannula was connected to an infusion pump (Harvard Apparatus, Natick Mass.) and a pressure transducer (Statham Gould, Cleveland, Ohio) through a 3 way stopcock to allow bladder filling and pressure measurement, respectively. The abdominal incision was covered with plastic wrap. A small incision was made in the perineum to allow placement of EMG electrodes into the periurethral musculature. EMG electrodes were also placed into the muscular tissue of the anus. EMG electrodes were connected to preamplifiers (Grass P511, Quincey, Mass.) with low and high pass filters set at 10 and 3000 HZ. EMG potentials were displayed on an oscilloscope (Gould 1602, Cleveland, Ohio) that was interfaced to a differential amplitude discriminator/ rate meter with wave-form discrimination capability (RAD III, Winston Electronics, Millbrae, Calif.). A catheter inserted into the carotid artery was connected to a pressure transducer (Statham Gould, Cleveland, Ohio) to record arterial pressure, which was used to trigger a heart rate meter (Biotach, Gould, Cleveland, Ohio). A catheter was inserted into the trachea to allow for artificial respiration and monitoring of expired $CO_2$ (Sensor Medics, Anaheim, Calif.). EMG potentials, rate meter output, bladder and arterial pressure, heart rate, and expired $CO_2$ measurements were recorded on a physiograph (Gould, TA4000, Cleveland, Ohio) and stored on an 8-channel digital audio tape recorder (SONY PC-108M, Tokyo, Japan).

After establishing control levels of anal and urethral activity, compounds were administered intravenously. Oxotremorine sesquifumarate (Sigma Chemicals, St. Louis, Mo.), atropine sulfate (RBI, Natick, Mo.), (−) scopolamine methyl bromide (RBI), physostigmine free base (Sigma Chemicals), neostigmine bromide (Sigma) and the test compounds were all dissolved in physiological saline.

The affinity of the compounds for the muscarinic receptors was determined using the non-selective agonist ligand, $^3$H-oxotremorine-M. Birdsdall N. J. M., Hulme E. C., and Burgen A. S. V., "The Character of Muscarinic Receptors in Different Regions of the Rat Brain", 207 *Proc. Roy. Soc.* 1 (London, Series B, 1980). The results of this assay are described in Table I below. Each compound was tested to determine the affinity of the compound for the muscarinic receptors using the following procedure.

For in vitro binding, male Sprague-Dawley (Harlan Sprague-Dawley, Indianapolis, Ind.) rats weighing from about 100 to about 150 grams each were sacrificed by decapitation. The brains were quickly removed and the cerebral cortex were dissected from the brain. The cerebral cortex tissue was homogenized in 10 volumes of 0.32M sucrose and homogenized for about 10 minutes at about 1000×g. The supernatant was centrifuged at about 12,000×g for about 10 minutes and the resulting pellet was resuspended in 20 mM tris-Cl, pH 7.4. The resuspended pellet was centrifuged again for about 10 minutes at about 50,000×g. The resulting homogenate was preincubated for about 10 minutes at about 25° C. and centrifuged again for about 10 minutes at about 50,000×g. The pellet was resuspended at 1 gram of pellet per 3 ml of buffer and frozen at about −80° C. until used.

The inhibition of binding of $^3$H-oxotremorine-M to muscarinic receptors was determined by mixing the compound of the Example, 3 nM $^3$H-oxotremorine-M (about 87 Ci/mmoles, New England Nuclear, Boston Mass.), and cerebral cortical membranes equivalent to about 10 mg wet weight, which is about 100 μg of cortical membrane protein, in about 1 ml total volume of 20 nM tris-Cl buffer, pH 7.4, containing 1 mM $MnCl_2$. The aforementioned homogenates mixture was incubated for about 15 minutes at about 25° C. and then the homogenates were filtered through glass filters (Whatman, GF/C) with vacuum. The filters were washed 3 times with about 2 ml of cold tris-Cl buffer, and placed in scintillation vials containing about 10 ml of scintillation fluid (Ready Protein+, Beckman, Fullerton, Calif.). Radioactivity trapped on the filters was determined by liquid scintillation spectrometry. Nonspecific binding was determined using 1 μM atropine. The concentration of compound required to inhibit specific binding 50% ($IC_{50}$) was determined using standardized computer assisted calculations (DeLean, A. et al. *Am. J. Physiol.*, 235, (1978)).

Test results obtained by testing some compounds of the present invention will appear from the following Table 1:

TABLE 1

| Compound No. | Inhibition of $^3$H-Oxo (nM) |
| --- | --- |
| 9 | 2.1 |
| 46 | 1.6 |
| 13 | 1.9 |
| 52 | 1.8 |
| 53 | 0.9 |
| 19 | 1.2 |
| 29 | 1.2 |
| 30 | 0.4 |
| 31 | 1.8 |
| 32 | 1.3 |
| 58 | 0.8 |
| 59 | 1.0 |

TABLE 1-continued

| Compound No. | Inhibition of $^3$H-Oxo (nM) |
| --- | --- |
| 56 | 0.4 |
| 74 | 1.4 |
| 76 | 7.7 |
| 77 | 2.7 |
| 82 | 1.3 |
| 133 | 1.3 |
| 102 | 4.5 |
| 103 | 2.7 |
| 104 | 2.6 |
| 131 | 2.8 |
| 106 | 2.8 |
| 107 | 1.0 |
| 111 | 1.0 |
| 112 | 0.6 |
| 113 | 0.89 |
| 114 | 0.45 |
| 119 | 0.9 |
| 120 | 0.9 |
| 121 | 1.0 |
| 122 | 2.1 |
| 130 | 1.8 |
| 157 | 10 |
| 158 | 10 |
| 167 | 0.76 |

The compounds used in this method are effective over a wide dosage range. For example, in the treatment of adult humans, dosages from about 0.05 to about 100 mg, preferably from about 0.1 to about 100 mg, per day may be used. A most preferable dosage is about 10 mg to about 70 mg per day. In choosing a regimen for patients suffering from urinary bladder dysfunctions it may frequently be necessary to begin with a dosage of from about 30 to about 70 mg per day and when the condition is under control to reduce the dosage as low as from about 1 to about 10 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, subcutaneous, intravenous, intraurethral, intramuscular, intranasal or an ointment, the oral route being preferred.

Typical compositions include a compound of formula I or a pharmaceutically acceptable acid addition salt thereof, associated with a pharmaceutically acceptable carrier. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethyl-cellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 1 to about 100 mg in a pharmaceutically acceptable carrier per unit dosage.

A typical tablet, appropriate for use in this method, may be prepared by conventional tabletting techniques and contains:

| Active compound | 5.0 mg |
|---|---|
| Lactose | 67.8 mg Ph. Eur. |
| Avicel ® | 31.4 mg |
| Amberlite ® | 1.0 mg |
| Magnesium stearate | 0.25 mg Ph. Eur. |

The compounds used in this method may be prepared by commonly known chemical methods. Most of the compounds may be prepared using the methods taught in PCT/DK91/00236 which are hereby incorporated by reference. The following description is intended to illustrate possible synthetic routes for the preparation of the compounds utilized in this method.

The compounds may be prepared by a) reacting a compound of formula II

wherein G has the meaning defined above, >=N is >—NH or; >=N and $R^6$ is H, OH or O-alkyl, with $S_2Cl_2$ to form a compound of formula III

wherein G has the meaning defined above; subsequent displacement of Cl with an appropriate nucleophile gives a compound of formula I wherein X is S, or b) dehydrating a compound of formula IV

wherein G has the meaning defined above and $R^7$ is alkyl, amino, halogen, alkoxy or alkylthio, to form a compound of formula V

wherein G and $R^7$ have the meanings defined above, or c) when $R^7$ in formula V is amino, the amino group can be substituted by chloro by known procedures, and subsequent displacement of Cl with an appropriate nucleophile gives a compound of formula I wherein X is O, or d) oxidizing a compound of formula VI

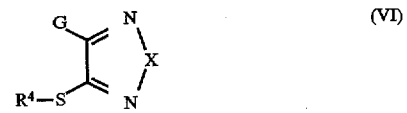

wherein G, $R^4$ and X have the meanings defined above by standard procedures to form a compound of formula VII

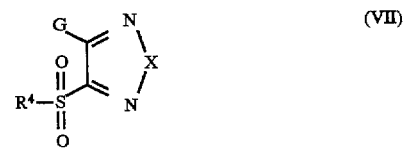

and subsequent displacement of —$SO_2$—$R^4$ with an appropriate nucleophile to form a compound of formula I.

It is to be understood that the invention extends to each of the stereoisomeric forms of the compounds of formula I as well as the racemates.

The following examples are included to more specifically describe the preparation of the compounds used in the method of this invention. The examples are not intended to limit the present invention in any way and should not be so construed.

EXAMPLE 1

A. Ethyl(1-azabicyclo[2.2.2]octan-3-ylidine)cyanoacetate

A solution of 3-quinuclidone (75 g, 0.6 mol), ammonium acetate (2.3 g, 30 mmol), acetic acid (3.75 ml) and ethyl cyanoacetate (67.8 g, 0.6 mol) in toluene (400 ml) was refluxed with a water separator for 18 h. Water (100 ml) and NaOH was added, and the mixture extracted several times with ether. The organic phases were dried and evaporated. The residue was purified by column chromatography (eluent: EtOAc/MeOH (2:1)), yielding 73 g of the title compound.

B. Ethyl(1-azabicyclo[2.2.2]octan-3-yl)cyanoacetate

A solution of ethyl(1-azabicyclo[2.2.2]octan-3-ylidene) cyanoacetate (73 g, 0.33 mol) in absolute ethanol (1 l) was treated with 10% palladium on charcoal (10 g) and hydrogen in a parr shaker at 20 psi for 5 h. Filtration and evaporation gave the wanted product in 68 g yield.

C. (1-Azabicyclo[2.2.2]octan-3-yl) hydroxyiminoacetonitrile

Ethyl(1-azabicyclo[2.2.2]octan-3-yl)cyanoacetate (10 g, 45 mmol) was added to a solution of sodium (1.04 g, 45 mmol) in absolute ethanol (60 ml). The mixture was stirred for 15 min. at room temperature and isoamylnitrite (7.9 ml, 60 mmol) was added. The reaction mixture was stirred for 18 h at 60° C. Evaporation of the reaction mixture gave crude title compound, which was used without further purification.

D. 3-Chloro-3-(3-chloro-1,2,5-thiadiazol-4-yl)-1-azabicyclo [2.2.2]octane oxalate To a solution of crude (1-azabicyclo[2.2.2]octan-3-yl) hydroxyiminoacetonitrile (max. 45 mmol) in DMF (60 ml) was slowly added a solution of $S_2Cl_2$ (10.85 ml, 135 mmol) in DMF (20 ml) at 0° C. After addition the reaction mixture was stirred at room temperature for 48 h. Water and 50%

NaOH was added to the ice cooled reaction mixture and extracted with ether. The combined ether phases were dried and evaporated. The residue was purified by column chromatography (eluent: EtOAc/MeOH (2:1)) to give the free base of the title compound in 1.04 g yield. Crystallization with oxalic acid from acetone gave an analytical pure product (Compound 1). M.p. 137°–139° C.

EXAMPLE 2

3-(3-Chloro-1,2,5-thiadiazol-4-yl)-3-hydroxy-1-azabicyclo[2.2.2]octane oxalate

A solution of 3-chloro-3-(3-chloro-1,2,5-thiadiazol-4-yl)-1-azabicyclo[2.2.2]octane (250 mg, 0.95 mmol) in ethanol (25 ml) was treated with formic acid (750 µl, 20 mmol), triethylamine (4.2 ml, 30 mmol) and 10% palladium on charcoal for 18 h at 60° C. After filtration and evaporation water and $K_2CO_3$ was added to the residue and extracted with ether. The dried ether phases were evaporated and purified by column chromatography (eluent: EtOAc/MeOH (2:1)). Crystallization as the oxalate from acetone gave the title compound in 150 mg yield. (Compound 2). M.p. 241°–242° C.

EXAMPLE 3

3-Methoxy-3-(3-methoxy-1,2,5-thiadiazol-4-yl)-1-azabicyclo[2.2.2]octane oxalate and 3-(3-Methoxy-1,2,5-thiadiazol-4-yl)-1-azabicyclo[2.2.2]oct-2-ene oxalate A solution of 3-chloro-3-(3-chloro-1,2,5-thiadiazol-4-yl)-1-azabicyclo[2.2.2]octane (500 mg, 1.9 mmol) and sodiummethoxide (20 mmol) in methanol(20 ml) was stirred for 48 h at 60° C. Water was added to the reaction mixture and extracted with ether. The combined organic phases were dried and evaporated. The two products were separated by column chromatography (eluent: EtOAc/MeOH (2:1)). Crystallization of the dimethoxy product as the oxalate from acetone gave 200 mg. (Compound 3). M.p. 113°–117° C. The monomethoxy oxalate was isolated in 60 mg yield (Compound 4). M.p. 143°–145° C.

EXAMPLE 4

3-(3-Hexyloxy-1,2,5-thiadiazol-4-yl)-1-azabicyclo[2.2.2]oct-2-ene oxalate, 3-Hexyloxy-3-(3-hexyloxy-1,2,5-thiadiazol-4-yl)-1-azabicyclo[2.2.2]octane oxalate and 3-(3-Hexyloxy-1,2,5-thiadiazol-4-yl)-3-hydroxy-1-azabicyclo[2.2.2]octane oxalate A 50% sodiumhydride dispersion (960 mg, 20 mmol) was dissolved in 1-hexanol and 3-chloro-3-(3-chloro-1,2,5-thiadiazol-4-yl)-1-azabicyclo[2.2.2]octane (500 mg, 1.9 mmol) was added. The reaction mixture was stirred at 90° C. for 18 h and evaporated. The residue was dissolved in water and extracted with ether. The dried ether phases were evaporated and the products separated by column chromatography (eluent: EtOAc/MeOH (2:1)). The first fractions contained the eliminated product which, after crystallization with oxalic acid, was collected in 70 mg yield. (Compound 5). M.p. 135°–137° C.

The next fractions contained the dihexyloxy analogue, which gave 70 mg as the oxalate salt. (Compound 6). M.p. 84°–85° C.

The later fractions gave the hydroxy-hexyloxy compound in 100 mg yield as the oxalate salt. (Compound 7). M.p. 145°–147° C.

EXAMPLE 5

3-(3-Chloro-1,2,5-thiadiazol-4-yl)-1-azabicyclo[2.2.2]octane oxalate

Hydrogenation for 48 h of 3-chloro-3-(3-chloro-1,2,5-thiadiazol-4-yl)-1-azabicyclo[2.2.2]octane (15.2 g, 66 mmol) in ethanol (500 ml) at 30 psi in the presence of 10% palladium on charcoal (2.0 g) gave, after filtration and evaporation, the hydrochloride salt of the wanted product in quantitative yield. Crystallization of a sample with oxalic acid from methanol/acetone/ether produced the title compound. (Compound 8). M.p. 207°–209° C.

EXAMPLE 6

3-(3-Ethoxy-1,2,5-thiadiazol-4-yl)-1-azabicyclo[2.2.2]octane fumarate

Sodium (200 mg, 8.7 mmol) was dissolved in ethanol (30 ml) and 3-(3-chloro-1,2,5-thiadiazol-4-yl)-1-azabicyclo[2.2.2]octane (300 mg, 1.3 mmol) was added. The reaction mixture was stirred at 60° C. for 18 h. Water was added and the reaction mixture extracted with ether. The dried and filtrated ether extracts were evaporated to give the free base. Crystallization as the fumarate salt from isopropanol/ether gave the title compound in 210 mg yield. (Compound 9). M.p. 128°–131° C.

EXAMPLE 7

The following compounds were made in exactly the same manner as described in example 6 using the appropriate alcohol:

3-(3-Propoxy-1,2,5-thiadiazol-4-yl)-1-azabicyclo[2.2.2]octane fumarate. (Compound 10). M.p. 64°–67° C.

3-(3-Butoxy-1,2,5-thiadiazol-4-yl)-1-azabicyclo[2.2.2]octane oxalate. (Compound 46). M.p. 159°–160° C.

EXAMPLE 8

3-(3-Hexyloxy-1,2,5-thiadiazol-4-yl)-1-azabicyclo[2.2.2]octane fumarate

A 50% dispersion of sodiumhydride (230 mg, 5 mmol) was dissolved in 1-hexanol (25 ml) and 3-(3-chloro-1,2,5-thiadiazol-4-yl)-1-azabicyclo[2.2.2]octane (250 mg, 1.1 mmol) was added. The reaction was stirred at 80° C. for 8 h and at room temperature for 18 h. After evaporation water was added to the residue and extracted with ether. The combined ether phases were dried and evaporated. Crystallization with fumaric acid from isopropanol/ether gave the title compound in 220 mg yield. (Compound 11). M.p. 108°–109° C.

The following compounds were made in exactly the same manner using the appropriate alcohol instead of 1-hexanol:

3-(3-(5-Hexenyloxy)-1,2,5-thiadiazol-4-yl)-1-azabicyclo[2.2.2]octane fumarate, M.p. 107°–110° C. (Compound 48).

3-(3-(3-Hexenyloxy)-1,2,5-thiadiazol-4-yl)-1-azabicyclo[2.2.2]octane fumarate, M.p. 135.5°–137.5° C. (Compound 49).

3-(3-Pentyloxy-1,2,5-thiadiazol-4-yl)-1-azabicyclo[2.2.2]octane oxalate, M.p. 102°–104° C. (Compound 50).

3-(3-Isopentyloxy-1,2,5-thiadiazol-4-yl)-1-azabicyclo[2.2.2]octane oxalate, M.p. 135.5°–137.5° C. (Compound 51).

EXAMPLE 9

3-(3-Pentylthio-1,2,5-thiadiazol-4-yl)-1-azabicyclo[2.2.2]octane fumarate

A solution of 3-(3-chloro-1,2,5-thiadiazol-4-yl)-1-azabicyclo[2.2.2]octane oxalate (500 mg, 1.56 mmol), sodiumhydrogen sulfide, monohydrate (463 mg, 6.25 mmol) and potassium carbonate (1.38 g, 10 mmol) in DMF (20 ml) was stirred at room temperature for 1 h. 1-Pentylbromide (755 mg, 5 mmol) was added, and the reaction mixture was stirred at room temperature for 18 h. 1N HCl was added, and the mixture extracted with ether once. 50% NaOH was added to the aqueous phase and extracted with ether. The ether phase was dried and evaporated. Crystallization of the residue with fumaric acid from isopropanol/ether gave the title compound in 380 mg yield. (Compound 12). M.p. 138°–139° C.

EXAMPLE 10

The following compounds were made in exactly the same manner as described in example 9, using the appropriate alkyl halogenide:

3-(3-Butylthio-1,2,5-thiadiazol-4-yl)-1-azabicyclo[2.2.2]octane fumarate. (Compound 13). M.p. 85°–87° C.

3-(3-Hexylthio-1,2,5-thiadiazol-4-yl)-1-azabicyclo[2.2.2]octane fumarate. (Compound 14). M.p. 138°–139° C.

3-(3-(3-Phenylpropylthio)-1,2,5-thiadiazol-4-yl)-1-azabicyclo[2.2.2]octane fumarate. (Compound 44). M.p. 123°–124° C.

3-(3-(4-Cyanobenzylthio)-1,2,5-thiadiazol-4-yl)-1-azabicyclo[2.2.2]octane oxalate. (Compound 45). M.p. 200° C. decomp.

3-(3-Ethylthio-1,2,5-thiadiazol-4-yl)-1-azabicyclo[2.2.2]octane oxalate, M.p. 194°–195° C. (Compound 52).

3-(3-Propylthio-1,2,5-thiadiazol-4-yl)-1-azabicyclo[2.2.2]octane oxalate, M.p. 206.5°–208° C. (Compound 53).

3-(3-Heptylthio-1,2,5-thiadiazol-4-yl)-1-azabicyclo[2.2.2]octane fumarate, M.p. 130°–132° C. (Compound 54).

EXAMPLE 11

A. Ethyl(1-azabicyclo[3.2.1]octan-6-ylidene)cyano acetate

A solution of 1-azabicyclo[3.2.1]octan-6-one (41.25 g, 0.33 mol), acetic acid (2 ml), ammonium acetate (1.25 g) and ethyl cyanoacetate (37 g, 0.33 mol) in toluene (500 ml) was refluxed with a Dean-Stark water separator for 40 h. The toluene phase was extracted with 3×200 ml 5M HCl solution. The water phase was basified with 28% ammonium hydroxide solution and extracted with ether (4×200 ml). The organic phases were dried over magnesium sulfate and evaporated. The residue was purified by column chromatography (eluent CH$_2$Cl$_2$/MeOH (9:1), yield 41 g of the title compound.

B. Ethyl(1-azabicyclo[3.2.1]octan-6-yl)cyanoacetate

A solution of ethyl(1-azabicyclo[3.2.1]octan-6-ylidene) cyanoacetate (41 g, 0.19 mol) in abs. ethanol (500 ml) was treated with 10% palladium on carbon (5 g) and hydrogen in a Parr shaker at 30 psi for 5 h. Filtration and evaporation gave the title compound in 36 g yield.

C. (1-azabicyclo[3.2.1]octan-6-yl)hydroxyiminoacetonitrile

Ethyl(1-azabicyclo[3.2.1]octan-6-yl)cyanoacetate (36 g, 0.16 mol) in abs. ethanol (100 ml) was added to a solution of sodium (4 g, 0.21 mol) in abs. ethanol (100 ml). Isoamylnitrite (25 ml, 0.19 mol) was added over 0.5 h, and the mixture was heated at 50° C. for 4 h. Evaporation of the reaction mixture gave crude sodium salt of the title compound, which was used without further purification.

D. 6-Chloro-6-(3-chloro-1,2,5-thiadiazol-4-yl)-1-azabicyclo[3.2.1]octane

A solution of crude (1-azabicyclo[3.2.1]octan-6-yl) hydroxyiminoacetonitrile (max. 0.16 mol) in DMF (150 ml) was added to a solution of S$_2$Cl$_2$ (50 ml, 0.68 mol) in DMF (100 ml) at 0° C. over 1 h. The reaction mixture was stirred over night and ice water (500 ml) was added. The mixture was filtered and the filter cake washed with 1M HCl (3×100 ml). The water solution was extracted with ether (2×200 ml), then basified with a 28% ammonium hydroxide solution and extracted with ether (4×200 ml). The combined ether extracts from the last extraction were dried and evaporated. The residue was purified by column chromatography (eluent: CH$_2$Cl$_2$/MeOH (9:1)) to give the title compound in 11 g yield as a mixture of the endo and exo forms.

EXAMPLE 12

The following compound was made in exactly the same manner as described in example 11, starting from 1-azabicyclo[2.2.1]heptan-3-one:

3-Chloro-3-(3-chloro-1,2,5-thiadiazol-4-yl)-1-azabicyclo[2.2.1]heptane.

EXAMPLE 13

Exo-6-(3-chloro-1,2,5-thiadiazol-4-yl)-1-azabicyclo[3.2.1]octane and Endo-6-(3-chloro-1,2,5-thiadiazol-4-yl)-1-azabicyclo[3.2.1]octane-oxalate A solution of Endo/Exo-6-chloro-6-(3-chloro-1,2,5-thiadiazol-4-yl)-1-azabicyclo[3.2.1]octane (1.3 g, 5 mmol) in abs. ethanol (100 ml) was treated with 10% palladium on carbon (300 mg) in a Parr shaker at 20 psi for 4 h. The solution was filtered and evaporated. The residue was purified by column chromatography with CH$_2$Cl$_2$/MeOH/TEA (9:1:0.25). The first fraction contained the exo compound, which after crystallization with oxalic acid in acetone, was collected in 150 mg yield. (Compound 15). M.p. 148°–149° C. The next fractions contained the endo compound, which after crystallization with oxalic acid from acetone was collected in 600 mg yield. (Compound 16). M.p. 195°–197° C.

EXAMPLE 14

Endo-6-(3-hexylthio-1,2,5-thiadiazol-4-yl)-1-azabicyclo[3.2.1]octane oxalate To a solution of endo-6-(3-chloro-1,2,5-thiadiazol-4-yl)-1-azabicyclo[3.2.1]octane (229 mg, 1.0 mmol) in DMF (10 ml) was added sodiumhydrogensulfide monohydrate (230 mg, 3.1 mmol). The reaction mixture was stirred at room temperature for 1 h. Potassium carbonate (1.38 g, 10 mmol) and 1-hexylbromide (335 mg, 2.5 mmol) was added and the mixture was stirred for 1 h. 1N HCl solution was added and the mixture extracted with ether (2×50 ml). The aqueous solution was basified with a 28% NH$_3$ solution and extracted with methylene chloride (3×100 ml). The methylene chloride phase was dried and evaporated. The residue was purified by column chromatography (eluent CH$_2$Cl$_2$/MeOH (9:1)). Crystallization of the pure base with oxalic acid from acetone gave the title compound in 100 mg yield. (Compound 17). M.p. 137°–139° C.

EXAMPLE 15

The following compounds were made in exactly the same manner as described in Example 14, using the appropriate alkyl bromide:

Endo-6-(3-(5-hexenylthio)-1,2,5-thiadiazol-4-yl)-1-azabicyclo[3.2.1]octane oxalate. (Compound 18). M.p. 113°–114° C.

Endo-6-(3-butylthio-1,2,5-thiadiazol-4-yl)-1-azabicyclo[3.2.1]octane oxalate. (Compound 24). M.p. 123°–124° C.

Endo-6-(3-ethylthio-1,2,5-thiadiazol-4-yl)-1-azabicyclo[3.2.1]octane oxalate. (Compound 25). M.p. 150°–151° C.

Endo-6-(3-pentylthio-1,2,5-thiadiazol-4-yl)-1-azabicyclo[3.2.1]octane oxalate. (Compound 26). M.p. 137°–138° C.

Endo-6-(3-(3-phenylpropylthio)-1,2,5-thiadiazol-4-yl)-1-azabicyclo[3.2.1]octane oxalate. (Compound 27). M.p. 127°–129° C.

Endo-6-(3-(4-cyanobenzylthio)-1,2,5-thiadiazol-4-yl)-1-azabicyclo[3.2.1]octane oxalate (Compound 28). M.p. 159°–161° C.

Endo-6-(3-propylthio-1,2,5-thiadiazol-4-yl)-1-azabicyclo[3.2.1]octane oxalate (Compound 57) M.p. 132°–134° C.

EXAMPLE 16

Exo-6-(3-ethoxy-1,2,5-thiadiazol-4-yl)-1-azabicyclo[3.2.1]octane oxalate and Endo-6-(3-ethoxy-1,2,5-thiadiazol-4-yl)-1-azabicyclo[3.2.1]octane oxalate To a solution of sodium (230 mg, 10 mmol) in abs. ethanol (20 ml) was added endo-6-(3-chloro-1,2,5-thiadiazol-4-yl)-1-azabicyclo[3.2.1]octane (229 mg, 1 mmol). The reaction mixture was heated at 50° C. for 12 h and evaporated. Water (100 ml) was added, and the mixture was extracted with methylene chloride (4×50 ml). The organic phases were dried and evaporated. The residue was purified by column chromatography eluent (CH$_2$Cl$_2$ MeOH/ TEA, 9:1:0.25). The first fractions contained the exo compound, which after crystallization with oxalic acid in acetone was collected in 50 mg yield. (Compound 19). M.p. 110°–112° C. The next fractions contained the endo compound, which after crystallization with oxalic acid in acetone was collected in 20 mg yield. (Compound 20). M.p. 127°–129° C.

EXAMPLE 17

Exo-3-(3-chloro-1,2,5-thiadiazol-4-yl)-1-azabicyclo[2.2.1]heptane oxalate and Endo-3-(3-chloro-1,2,5-thiadiazol-4-yl)-1-azabicyclo[2.2.1]heptane oxalate A solution of endo/exo-3-chloro-3-(3-chloro-1,2,5-thiadiazol-4-yl)-1-azabicyclo[2.2.1]heptane (0.5 g, 2 mmol) in abs. ethanol (100 ml) was treated with 10% palladium on carbon in a Parr shaker at 20 psi for 4 h. The solution was filtered and evaporated. The residue was purified by column chromatography, eluent CH$_2$Cl$_2$/MeOH (9:1). The first fractions contained the exo compound, which after crystallization with oxalic acid from acetone/ether was collected in 50 mg yield. (Compound 21). M.p. 138°–140° C. The next fractions contained the endo compound, which after crystallization with oxalic acid from acetone, was collected in 450 mg yield. (Compound 22). M.p. 118°–121° C.

EXAMPLE 18

Endo-3-(3-methoxy-1,2,5-thiadiazol-4-yl)-1-azabicyclo[2.2.1]heptane oxalate

To a solution of sodium (110 mg, 5 mmol) in methanol (20 ml) was added endo-3-(3-chloro-1,2,5-thiadiazol-4-yl)-1-azabicyclo[2.2.1]heptane (110 mg, 0.5 mmol). The reaction mixture was heated at reflux for 60 h and evaporated. Water (50 ml) was added, and the mixture was extracted with methylene chloride (4×50 ml). The organic phases were dried and evaporated. The residue was purified by column chromatography eluent (CH$_2$Cl$_2$/MeOH, 9:1). Crystallization of the free base with oxalic acid from acetone/ether gave the title compound in 40 mg yield. (Compound 23). M.p. 104°–106° C.

EXAMPLE 19

Exo-6-(3-hexylthio-1,2,5-thiadiazol-4-yl)-1-azabicyclo[3.2.1]octane oxalate

To a solution of exo-6-(3-chloro-1,2,5-thiadiazol-4-yl)-1-azabicyclo[3.2.1]octane (229 mg, 1.0 mmol) in DMF (20 ml) was added sodiumhydrogensulfide monohydrate (230 mg, 3.0 mmol). The reaction mixture was stirred at room temperature for 1 h. Potassium carbonate (1.38 g, 10 mmol) and 1-hexylbromide (335 mg, 2.5 mmol) was added and the mixture was stirred for 1 h. 1N HCl solution was added and the mixture extracted with ether (2×50 ml). The aqueous solution was basified with a 28% NH$_3$ solution and extracted with ether (2×50 ml). The ether phase was dried and evaporated. The residue was crystallized as the oxalate salt from acetone/ether in 200 mg yield. (Compound 29). M.p. 118°–119° C.

EXAMPLE 20

The following compounds were made in exactly the same manner as described in example 19, using the appropriate alkylbromide:

Exo-6-(3-butylthio-1,2,5-thiadiazol-4-yl)-1-azabicyclo[3.2.1]octane oxalate. (Compound 30). M.p. 143°–145° C.

Exo-6-(3-pentylthio-1,2,5-thiadiazol-4-yl)-1-azabicyclo[3.2.1]octane oxalate. (Compound 31). M.p. 117°–118° C.

Exo-6-(3-ethylthio-1,2,5-thiadiazol-4-yl)-1-azabicyclo[3.2.1]octane oxalate. (Compound 32). M.p. 159°–160° C.

Exo-6-(3-propylthio-1,2,5-thiadiazol-4-yl)-1-azabicyclo[3.2.1]octane oxalate (Compound 58), M.p. 173°–174° C.

EXAMPLE 21

Endo-3-(3-pentylthio-1,2,5-thiadiazol-4-yl)-1-azabicyclo[2.2.1]heptane fumarate

To a solution of endo-3-(3-chloro-1,2,5-thiadiazol-4-yl)-1-azabicyclo[2.2.1]heptane (215 mg, 1.0 mmol) in DMF (20 ml) was added sodium hydrogensulfide monohydrate (230 mg, 3.0 mmol). The reaction mixture was stirred at room temperature for 1 h. Potassium carbonate (1.38 g, 10 mmol) and 1-pentylbromide (0.45 g, 3 mmol) was added and the mixture was stirred for 1 h. 1M hydrochloric acid solution (100 ml) was added and the mixture extracted with ether (2×50 ml). The aqueous solution was basified with a 28% NH$_3$-solution and extracted with ether (3×75 ml). The ether phase was dried and evaporated. The residue was crystallized as the fumarate salt from MeOH/ether in 250 mg yield. (Compound 33). M.p. 120°–122° C.

EXAMPLE 22

The following compounds were made in exactly the same manner as described in example 21 using the appropriate alkylbromide:

Endo-3-(3-hexylthio-1,2,5-thiadiazol-4-yl)-1-azabicyclo[2.2.1]heptane fumarate. (Compound 34). M.p. 127°–129° C.

Endo-3-(3-(3-phenylpropylthio)-1,2,5-thiadiazol-4-yl)-1-azabicyclo[2.2.1]heptane oxalate. (Compound 35). M.p. 119°–120° C.

Endo-3-(3-butylthio-1,2,5-thiadiazol-4-yl)-1-azabicyclo[2.2.1]heptane fumarate. (Compound 36). M.p. 106°–108° C.

Endo-3-(3-propylthio-1,2,5-thiadiazol-4-yl)-1-azabicyclo[2.2.1]heptane oxalate. (Compound 37). M.p. 169°–170° C.

EXAMPLE 23

Exo-3-(3-pentylthio-1,2,5-thiadiazol-4-yl)-1-azabicyclo[2.2.1]heptane oxalate

To a solution of exo-3-(3-chloro-1,2,5-thiadiazol-4-yl)-1-azabicyclo[2.2.1]heptane (215 mg, 1.0 mmol) in DMF (20 ml) was added sodium hydrogensulfide monohydrate (230 mg, 3.0 mmol). The reaction mixture was stirred at room temperature for 1 h. Potassium carbonate (1.38 g, 10 mmol) and 1-pentylbromide (0.45 g, 3 mmol) was added and the mixture was stirred for 1 h. 1M hydrochloric acid solution (100 ml) was added and the mixture extracted with ether (2×50 ml). The aqueous solution was basified with a 28% $NH_3$-solution and extracted with ether (3×75 ml). The ether phase was dried and evaporated. The residue was crystallized as the oxalate salt from MeOH/ether in 250 mg yield. (Compound 38). M.p. 120°–122° C.

EXAMPLE 24

The following compounds were made in exactly the same manner as described in example 23, using the appropriate alkylbromide:

Exo-3-(3-hexylthio-1,2,5-thiadiazol-4-yl)-1-azabicyclo[2.2.1]heptane oxalate. (Compound 39). M.p. 102°–103° C.

Exo-3-(3-propylthio-1,2,5-thiadiazol-4-yl)-1-azabicyclo[2.2.1]heptane oxalate. (Compound 40). M.p. 132°–133° C.

Exo-3-(3-(3-phenylpropylthio)-1,2,5-thiadiazol-4-yl)-1-azabicyclo[2.2.1]heptane oxalate. (Compound 41). M.p. 126°–127° C.

Exo-3-(3-butylthio-1,2,5-thiadiazol-4-yl)-1-azabicyclo[2.2.1]heptane oxalate. (Compound 42). M.p. 188°–189° C.

EXAMPLE 25

A. 8-Ethoxycarbonyl-3-chloro-2-formyl-8-azabicyclo[3.2.1]oct-2-ene

To a solution of dry DMF (45 g, 0.6 mol) in dry $CH_2Cl_2$ (150 ml) was added $POCl_3$ (75 g, 0.5 mol) at 0°–10° C. 8-Ethoxycarbonyl-8-azabicyclo[3.2.1]octane-3-one (57 g, 0.29 mol) dissolved in dry $CH_2Cl_2$ (60 ml) was added. The reaction mixture was stirred over night at room temperature, then added to ice water (1.000 ml). The phases were separated and the water phase extracted with $CH_2Cl_2$ (2×200 ml). The combined $CH_2Cl_2$ extracts were washed with a saturated $NaHCO_3$ solution and water, dried and evaporated to give 70 g of the title compound, which was used in the next step without further purification.

B. 8-Ethoxycarbonyl-3-chloro-2-(3-chloro-1,2,5-thiadiazol-4-yl)-8-azabicyclo[3,2,1]oct-2-ene Potassium cyanide (8.5 g, 0.13 mol) and ammonium chloride (6.4 g, 0.12 mol) were dissolved in a min. amount of water. 8-Ethoxycarbonyl-3-chloro-2-formyl-8-azabicyclo[3.2.1]oct-2-ene (23 g, 0.1 mol) dissolved in DMF (25 ml) was added. The reaction mixture was stirred at room temperature for 3 days, then added to a 5N hydrochloric acid solution (200 ml). The aqueous phase was extracted with ether (3×75 ml), then basified with a 28% $NH_3$ solution and extracted with ether (4×100 ml). The ether phases from the last extraction were dried, evaporated and dissolved in DMF (50 ml). This solution was added to sulphur monochloride (16.8 g, 0.12 mol) in DMF (50 ml). The reaction mixture was stirred over night at room temperature and poured into ice-water. The water phase was extracted with ether (3×100 ml). The combined ether phases were dried and evaporated. The residue was purified by column chromatography (eluent: $CH_2Cl_2$). Yield 3.2 g as an oil.

EXAMPLE 26

3-Chloro-2-(3-ethoxy-1,2,5-thiadiazol-4-yl)-8-azabicyclo[3.2.1]oct-2-ene oxalate To a solution of sodium (230 mg, 10 mmol) in abs. ethanol (50 ml) was added 8-ethoxycarbonyl-3-chloro-2-(3-chloro-1,2,5-thiadiazol-4-yl)-8-azabicyclo[3.2.1]oct-2-ene (670 mg, 2 mmol). The reaction mixture was heated at reflux overnight, evaporated and conc. HCl (40 ml) was added. The reaction mixture was heated at reflux for 4 days, evaporated and basified with a 28% $NH_3$ solution. The aqueous solution was extracted with ether (3×75 ml). The combined ether extracts were dried and evaporated. The residue was purified by column chromatography (eluent $CH_2Cl_2$/MeOH-9:1). Crystallization of the free base with oxalic acid in acetone gave the title compound in 110 mg yield. (Compound 43). M.p. 178°–180° C.

EXAMPLE 27

3-Chloro-2-(3-chloro-1,2,5-thiadiazol-4-yl)-8-azabicyclo[3.2.1]oct-2-ene oxalate To a solution of 8-Ethoxycarbonyl-3-chloro-2-(3-chloro-1,2,5-thiadiazol-4-yl)-8-azabicyclo[3.2.1]oct-2-ene (1.7 g, 5 mmol) in dry toluene (50 ml) was added $AlCl_3$ (2.6 g, 20 mmol). The reaction mixture was slowly heated to 80° C. and kept at this temperature for 10 min. After cooling to room temperature the reaction mixture was poured on ice and basified with a 50% NaOH solution. The aqueous phase was extracted with $CH_2Cl_2$ (3×100 ml). The combined organic extracts were dried over $MgSO_4$ and evaporated. The residue was crystallized as the oxalate salt from acetone to give the title compound. Yield 1.6 g (Compound 47), M.p. 194°–195° C.

EXAMPLE 28

The following compounds were made in exactly the same manner as described in Example 16 using the appropriate alcohol:

Exo-6-(3-pentyloxy-1,2,5-thiadiazol-4-yl)-1-azabicyclo[3.2.1]octane oxalate (Compound 59), M.p. 122°–123° C.

Endo-6-(3-pentyloxy-1,2,5-thiadiazol-4-yl)-1-azabicyclo[3.2.1]octane oxalate (Compound 60), M.p. 124°–125° C.

EXAMPLE 29

A. 4-Chloro-3-formyl-1-azabicyclo[3.3.1]non-2-ene

To DMF (50 ml, 0.68 mol) was slowly added POCl₃ (50 ml, 0.54 mol) at 0° C. over 1 h. 1-Azabicyclo[3.3.1]nonane-4-one hydrochloride (17.5 g, 0.1 mol) was added in one portion and the reaction mixture heated at 100° C. for 1 h. After cooling the reaction mixture was poured on ice (1000 g) and the reaction mixture neutralized with potassium carbonate. The water phase was extracted with ether (5×200 ml). The organic phase was dried over MgSO₄ and evaporated. The residue was purified by column chromatography (eluent: CH₂Cl₂/CH₃OH (9:1)), yielding 17 g of the title compound.

B. 4-Chloro-3-(3-chloro-1,2,5-thiadiazol-4-yl)-1-azabicyclo[3.3.1]non-3-ene oxalate To a solution of oxalic acid (9.0 g, 100 mmol) in water (100 ml) was added 4-chloro-3-formyl-1-azabicyclo[3.3.1]non-2-ene (17.0 g, 95 mmol). Potassium cyanide (6.8 g, 10 mmol) dissolved in a min. amount of water was added dropwise. The reaction mixture was stirred at room temperature for 2 h. The precipitated crystals were filtered and suspended in water/EtOH (4:1, 120 ml). Ammonium chloride (6.0 g, 100 mmol) and ammonium hydroxide (28% in water 10 ml) was added and the reaction mixture was stirred at room temperature overnight. The water phase was extracted with methylene chloride (5×100 ml). The organic phases were dried over magnesium sulphate and evaporated. The residue was dissolved in DMF (50 ml) and added dropwise to a solution of sulfurmonochloride (20 ml, 250 mmol) in DMF (30 ml) at 0° C. The reaction mixture was stirred at room temperature for 4 h, then crushed ice (500 g) was added. The precipitated sulfur was filtered off and the filtrate washed with 1M hydrochloric acid solution (2×100 ml) the combined water phases was basified with ammonia (28% in water) and extracted with ether (4×200 ml). The combined organic phases were dried and evaporated. The residue was crystallized as the oxalate salt from acetone/ether to give the title compound. Yield 10.8 g (Compound 61), M.p. 149°–150° C.

EXAMPLE 30

4-Chloro-3-(3-propyloxy-1,2,5-thiadiazol-4-yl)-1-azabicyclo[3.3.1]non-3-ene oxalate To a solution of sodium (0.23 g, 10 mmol) in n-propanol (10 ml) was added 4-chloro-3-(3-chloro-1,2,5-thiadiazol-4-yl)-1-azabicyclo[3.3.1]non-3-ene (0.274 g, 1 mmol). The reaction mixture was heated at 60° C. for 2 h. Hydrochloric acid (1M, 100 ml) was added, and the water phase extracted with ether (2×50 ml). The water phase was basified with solid potassium carbonate and extracted with ether (3×75 ml). The combined ether extracts were dried over magnesium sulfate and evaporated. The residue was crystallized as the oxalate salt from acetone/ether to give the title compound. Yield 180 mg (Compound 62), M.p. 122°–123° C.

EXAMPLE 31

The following compounds were made in exactly the same manner as described in example 30 using the appropriate alcohol:

4-Chloro-3-(3-pentyloxy-1,2,5-thiadiazol-4-yl)-1-azabicyclo[3.3.1]non-3-ene oxalate (Compound 63), M.p. 114°–115° C.

4-Chloro-3-(3-methoxy-1,2,5-thiadiazol-4-yl)-1-azabicyclo[3.3.1]non-3-ene oxalate (Compound 64), M.p. 103°–104° C.

EXAMPLE 32

4-Chloro-3-(1,2,5-thiadiazol-4-yl)-1-azabicyclo[3.3.1]non-3-ene oxalate

To a solution of sodium (0.092 g, 4 mmol) in isopropanol (40 ml) was added n-butylmercaptan (270 ml, 3 mmol). 4-Chloro-3-(3-chloro-1,2,5-thiadiazol-4-yl)-1-azabicyclo[3.3.1]non-3-ene (0.82 g, 3 mmol) dissolved in isopropanol (10 ml) was added and the reaction mixture was stirred overnight at room temperature. The reaction mixture was evaporated and hydrochloric acid (1M, 100 ml) was added. The water phase was extracted with ether (2×50 ml) basified with solid potassium carbonate and extracted with ether (3×75 ml). The organic phase was dried and evaporated. The residue was purified by column chromatography (eluent: ethyl acetate) and the free base was crystallized with oxalic acid from acetone to give the title compound. Yield 250 mg (Compound 65) M.p. 175°–77° C.

EXAMPLE 33

(−)3-(3-Butylthio-1,2,5-thiadiazol-4-yl)-1-azabicyclo[2.2.2]octane (+)L-tartrate To a solution of 3-(3-butylthio-1,2,5-thiadiazol-4-yl)-1-azabicyclo[2.2.2]octane (free base of compound 13, example 10) (5.5 g, 19.43 mmol) in ethanol (50 ml) was added a solution of (+)L-tartaric acid (2.9 g, 19.4 mmol) in water (10 ml). Ether (approx. 200 ml) was added to the solution to give a slightly unclear solution. The title compound was precipitated overnight and the crystals collected by filtration (3.05 g). Recrystallization twice from ethanol (20 ml) and ether gave the pure (−)enantiomer (1.90 g) (Compound 55), M.p. 106°–108° C. [α](free base)=−15.80° (C=4.05 MeOH).

EXAMPLE 34

(+)3-(3-Butylthio-1,2,5-thiadiazol-4-yl)-1-azabicyclo[2.2.2]octane (−)D-tartrate The mother liquour from the crystallization with (+)L-tartaric acid (example 33) was evaporated and the residue treated with 50% NaOH in water and extracted with ether. The combined ether phase were dried and evaporated to give crude free base of the title compound (2.9 g, 10.2 mmol). The residue was dissolved in ethanol (15 ml) and a solution of (−)D-tartaric acid (1.54 g, 10.2 mmol) in water (4 ml) was added. Ether was added to the solution and the title compound precipitated overnight. The crystals were collected by filtration and recrystallization twice from ethanol/ether gave the pure (+)enantiomer (1.90 g) (Compound 56), M.p. 106°–108° C. [α](free base)=+14.94° (C=4.09 in MeOH).

EXAMPLE 35

3-(3-Amino-1,2,5-oxadiazol-4-yl)-1-azabicyclo[2.2.2]octane fumarate

To a solution of crude (1-azabicyclo[2.2.2]octan-3-yl) hydroxyiminoacetonitrile (10 g, max. 29 mmol) (example 1C) in methanol (50 ml) was added a methanol solution of hydroxylamine (prepared from NH₂OH, HCl (4.2 g, 60 mmol) in methanol (60 ml) and sodium (1.38 g, 60 mmol) in methanol (60 ml). The reaction mixture was stirred at 40° C. for 18 h and evaporated to give the crude amide oxime derivative. The residue was treated with excess of POCl₃ at 45° C. for 18 h. Water and sodium hydroxide was added to obtain alkaline pH and the aqueous mixture extracted with chloroform. The combined organic phases were dried and evaporated to give the free base of the title compound as a solid (yield 570 mg). MS: M⁺: 194. Crystallization as the fumarate salt from isopropanol gave the title compound (110 mg) (Compound 66), M.p. 60°–75° C.

EXAMPLE 36

A. 5-Carboxaldehyde-1-azabicyclo[3.2.1]octane

To a solution of 1-azabicyclo[3.2.1]oct-5-yl-N-methyl-N-methoxycarboxamide (4.0 g, 17.4 mmol) in tetrahydrofuran (100 ml) was added dropwise a 1 Molar solution of DIBAL (26 ml, 26 mmol) at −65° C. The temperature of the reaction mixture was allowed to raise to 0° C. over 30 min. and then cooled to −65° C. Aqueous hydrochloric acid (75 ml, 5N) was added to the cold reaction mixture and the tetrahydrofuran was evaporated in vacuo. The aqueous residue was stirred overnight at room temperature and then evaporated. Water and potassium carbonate was added to the residue and extracted with methylene chloride (3×300 ml). The combined methylene chloride phases were dried and evaporated to give the title compound as an oil. Yield 2.75 g.

B. 2-Amino-2-(1-azabicyclo[3.2.1]oct-5-yl)acetonitrile

To a solution of potassium cyanide (1.43 g, 22 mmol) in water (20 ml) 5-carboxaldehyde-1-azabicyclo[3.2.1]octane (2.75 g, 19.8 mmol) was added over 30 min. at 0°–10° C. Acetic acid (1.26 ml, 22 mmol) was added to the reaction mixture over 30 min. at 5°–10° C. The reaction mixture was stirred at room temperature for further 18 h and cooled to 5° C. Aqueous sodium hydroxide was added to obtain alkaline pH and then extracted with methylene chloride (3×200 ml). The combined organic phases were evaporated and the residue was treated with a solution of ammonium chloride (3.8 g, 72 mmol) in water (10 ml) and 25% aqueous ammonia (5 ml). The reaction mixture was stirred at room temperature for 18 h and then extracted with methylene chloride. The combined organic phases were dried and evaporated to give the title compound. Yield. 1.67 g.

C. 5-(3-Chloro-1,2,5-thiadiazol-4-yl)-1-azabicyclo[3.2.1]octane oxalate

2-Amino-2-(1-azabicyclo[3.2.1]oct-5-yl)acetonitrile (1.67 g, 10 mmol) was dissolved in DMF (10 ml) and a solution of sulfur monochloride (2.57 ml, 30 mmol) in DMF (10 ml) was added dropwise at 0° C. The reaction mixture was stirred at room temperature for 18 h and cooled to 0° C. whereupon water (40 ml) and aqueous potassium hydroxide was added slowly. The alkaline reaction mixture was extracted with ether (3×300 ml) and the combined ether phases were dried and evaporated. The residue (850 mg) was crystallized with oxalic acid from acetone/methanol to give the title compound. Yield 710 mg (Compound 67), M.p. 137.5°–139.5° C.

EXAMPLE 37

5-(3-Hexylthio-1,2,5-thiadiazol-4-yl)-1-azabicyclo[3.2.1]octane oxalate

Sodium hydrosulfide monohydrate (326 mg, 4.4 mmol) was added to a solution of 5-(3-chloro-1,2,5-thiadiazol-4-yl)-1-azabicyclo[3.2.1]octane oxalate (350 mg, 1.1 mmol) in DMF (20 ml) at room temperature and the reaction mixture was stirred for 30 min. Potassium carbonate (1.24 g, 9 mmol) and 1-bromohexane (561 μl, 4 mmol) were added and the reaction mixture was stirred for 3 h. Water (50 ml) was added to the reaction mixture and the aqueous phase extracted with ether (3×200 ml). The combined ether phases were dried and evaporated to give the crude free base of the title compound (220 mg). The residue was crystallized as the oxalate salt from acetone to give the title compound. Yield 200 mg (Compound 68), M.p. 67°–69° C.

EXAMPLE 38

Exo-3-(3-methylthio-1,2,5-thiadiazol-4-yl)-1-azabicyclo[2.2.1]heptane oxalate To a solution of exo-3-(3-chloro-1,2,5-thiadiazol-4-yl)-1-azabicyclo[2.2.1]heptane (215 mg, 1.0 mmol) in DMF (20 ml) was added sodiumhydrogensulfide monohydrate (230 mg, 3.0 mmol). The reaction mixture was stirred at room temperature for 1 h. Potassium carbonate (1.38 g, 10 mmol) and methyliodide (0.42 g, 3 mmol) were added and the mixture stirred at room temperature for 0.5 h. 1N hydrochloric acid solution (100 ml) was added and extracted with ether (2×50 ml). The aqueous solution was basified with a 28% $NH_3$ solution and extracted with ether (3×75 ml). The combined ether phases were dried and evaporated. The residue was crystallized as the oxalate salt from acetone in 180 mg yield. (Compound 69). M.p. 133°–139° C.

EXAMPLE 39

The following compound was made in exactly the same manner as described in example 38, using ethyliodide:

Exo-3-(3-ethylthio-1,2,5-thiadiazol-4-yl)-1-azabicyclo[2.2.1]heptane oxalate from ethyliodide and exo-3-(3-chloro-1,2,5-thiadiazol-4-yl)-1-azabicyclo[2.2.1]heptane. (Compound 70). M.p. 156°–157° C.

Exo-3-(3-(4-cyanobenzylthio)-1,2,5-thiadiazol-4-yl)-1-azabicyclo[2.2.1]heptane oxalate from exo-3-(3-chloro-1,2,5-thiadiazol-4-yl)-1-azabicyclo[2.2.1]-heptane and 4-cyanobenzylchloride. (Compound 173). M.p. 200°–201° C.

EXAMPLE 40

The following compounds were made in exactly the same manner as described in example 38 using endo 3-(3-chloro-1,2,5-thiadiazol-4-yl)-1-azabicyclo[2.2.1]heptane and the appropriate alkylhalogenide.

Endo-3-(3-(2-phenoxyethylthio)-1,2,5-thiadiazol-4-yl)-1-azabicyclo[2.2.1]heptane oxalate from 2-phenoxyethylbromide and endo 3-(3-chloro-1,2,5-thiadiazol-4-yl)-1-azabicyclo[2.2.1]heptane. (Compound 71). M.p. 127°–130° C.

Endo-3-(3-(2-thienyl)propylthio-1,2,5-thiadiazol-4-yl)-1-azabicyclo[2.2.1]heptane oxalate from 1-chloro-3-(2-thienyl)propane and endo-3-(3-chloro-1,2,5-thiadiazol-4-yl)-1-azabicyclo[2.2.1]heptane. (Compound 72). M.p. 123°–126° C.

Endo-3-(3-(2-phenylthio)ethylthio-1,2,5-thiadiazol-4-yl)-1-azabicyclo[2.2.1]heptane oxalate from 1-chloro-2-(phenylthio)ethane and endo-3-(3-chloro-1,2,5-thiadiazol-4-yl)-1-azabicyclo[2.2.1]heptane. (Compound 73). M.p. 143°–145° C.

EXAMPLE 41

Exo-6-(3-methylthio-1,2,5-thiadiazol-4-yl)-1-azabicyclo[3.2.1]octane oxalate To a solution of exo-6-(3-chloro-1,2,5-thiadiazol-4-yl)-1-azabicyclo[3.2.1]octane (229 mg, 1.0 mmol) in DMF (20 ml) was added sodiumhydrogensulfide monohydrate (230 mg, 3.0 mmol). The reaction mixture was stirred at room temperature for 1 h. Potassium carbonate (1.38 g, 10 mmol) and methyliodide (0.42 g, 3 mmol) were added and the mixture stirred for 1 h. 1N hydrochloric acid solution (100 ml) was added and the mixture extracted with ether (2×50 ml). The aqueous solution was basified with a 28% $NH_3$ solution and extracted with ether (3×75 ml). The combined ether phases were dried and evaporated. The residue was crystallized as the oxalate salt from acetone in 200 mg yield. (Compound 74). M.p. 141°–142° C.

EXAMPLE 42

The following compounds were made in exactly the same manner as described in example 41 using the appropriate alkylhalogenide:

Exo-6-(3-heptylthio-1,2,5-thiadiazol-4-yl)-1-azabicyclo [3.2.1]octane oxalate from exo-6-(3-chloro-1,2,5-thiadiazol-4-yl)-1-azabicyclo[3.2.1]octane and 1-bromoheptane. (Compound 75). M.p. 111°–112° C.

Exo-6-(3-isohexylthio-1,2,5-thiadiazol-4-yl)-1-azabicyclo [3.2.1]octane oxalate from exo-6-(3-chloro-1,2,5-thiadiazol-4-yl)-1-azabicyclo[3.2.1]octane and 1-bromo-4-methylpentane. (Compound 76). M.p. 128°–130° C.

Exo-6-(3-isopentylthio-1,2,5-thiadiazol-4-yl)-1-azabicyclo [3.2.1]octane from exo-6-(3-chloro-1,2,5-thiadiazol-4-yl) -1-azabicyclo[3.2.1]octane and 1-bromo-3-methylbutane. (Compound 77). M.p. 130°–132° C.

Exo-6-(3-(4-cyanobutylthio)-1,2,5-thiadiazol-4-yl)-1-azabicyclo[3.2.1]octane oxalate from exo-6-(3-chloro-1, 2,5-thiadiazol-4-yl)-1-azabicyclo[3.2.1]octane and 1-bromo-4-cyanobutane. (Compound 78). M.p. 148°–150° C.

Exo-6-(3-cyanomethylthio-1,2,5-thiadiazol-4-yl)-1-azabicyclo[3.2.1]octane oxalate from exo-6-(3-chloro-1, 2,5-thiadiazol-4-yl)-1-azabicyclo[3.2.1]octane and chloroacetonitrile. (Compound 79). M.p. 141°–142° C.

Exo-6-(3-(2-cyanoethylthio)-1,2,5-thiadiazol-4-yl)-1-azabicyclo[3.2.1]octane oxalate from exo-6-(3-chloro-1, 2,5-thiadiazol-4-yl)-1-azabicyclo[3.2.1]octane and 1-bromo-2-cyanoethane. (Compound 80). M.p. 151°–152° C.

Exo-6-(3-(3-cyanopropylthio)-1,2,5-thiadiazol-4-yl)-1-azabicyclo[3.2.1]octane oxalate from exo-6-(3-chloro-1, 2,5-thiadiazol-4-yl)-1-azabicyclo[3.2.1]octane and 1-bromo-3-cyanopropane. (Compound 81). M.p. 114°–115° C.

Exo-6-(3-(4-cyanobenzylthio)-1,2,5-thiadiazol-4-yl)-1-azabicyclo[3.2.1]octane oxalate from exo-6-(3-chloro-1, 2,5-thiadiazol-4-yl)-1-azabicyclo[3.2.1]octane and 4-cyanobenzylchloride. (Compound 82). M.p. 198°–199° C.

Exo-6-(3-(3-phenylpropylthio)-1,2,5-thiadiazol-4-yl)-1-azabicyclo[3.2.1]octane oxalate from exo-6-(3-chloro-1, 2,5-thiadiazol-4-yl)-1-azabicyclo[3.2.1]octane and 1-bromo-3-phenylpropane. (Compound 83). M.p. 149°–150° C.

Exo-6-(3-(2-phenoxyethylthio)-1,2,5-thiadiazol-4-yl)-1-azabicyclo[3.2.1]octane oxalate from exo-6-(3-chloro-1, 2,5-thiadiazol-4-yl)-1-azabicyclo[3.2.1]octane and 1-bromo-2-phenoxyethane. (Compound 133). M.p. 137°–144° C.

Exo-6-(3-benzylthio-1,2,5-thiadiazol-4-yl)-1-azabicyclo [3.2.1]octane oxalate from exo-6-(3-chloro-1,2,5-thiadiazol-4-yl)-1-azabicyclo[3.2.1]octane and benzylchloride. (Compound 134). M.p. 153°–155° C.

Exo-6-(3-(2-cyanobenzylthio)-1,2,5-thiadiazol-4-yl)-1-azabicyclo[3.2.1]octane oxalate (Compound 223) M.p. 107°–110° C. from exo-6-(3-chloro-1,2,5-thiadiazol-4-yl) -1-azabicyclo[3.2.1]octane and 2-cyanobenzylbromide.

Exo-6-(3-(3-cyanobenzylthio)-1,2,5-thiadiazol-4-yl)-1-azabicyclo[3.2.1]octane oxalate (Compound 224) M.p. 154°–156° C. from exo-6-(3-chloro-1,2,5-thiadiazol-4-yl) -1-azabicyclo[3.2.1]octane and 3-cyanobenzylbromide.

Exo-6-(3-(2-trifluoromethylbenzylthio)-1,2,5-thiadiazol-4-yl)-1-azabicyclo[3.2.1]octane oxalate (Compound 225) M.p. 135°–138° C. from exo-6-(3-chloro-1,2,5-thiadiazol-4-yl)-1-azabicyclo[3.2.1]octane and 2-trifluoromethylbenzylbromide.

Exo-6-(3-(3-trifluoromethylbenzylthio)-1,2,5-thiadiazol-4-yl)-1-azabicyclo[3.2.1]octane oxalate (Compound 226) M.p. 152°–155° C. from exo-6-(3-chloro-1,2,5-thiadiazol-4-yl)-1-azabicyclo[3.2.1]octane and 3-trifluoromethylbenzylbromide.

EXAMPLE 43

The following compounds were made in exactly the same manner as described in example 41 by reacting endo-6-(3-chloro-1,2,5-thiadiazol-4-yl)-1-azabicyclo[3.2.1]octane with the appropriate alkylhalogenide:

Endo-6-(3-(2-phenoxyethylthio)-1,2,5-thiadiazol-4-yl)-1-azabicyclo[3.2.1]octane oxalate from endo-6-(3-chloro-1, 2,5-thiadiazol-4-yl)-1-azabicyclo[3.2.1]octane and 1-bromo-2-phenoxyethane. (Compound 84). M.p. 150°–155° C.

Endo-6-(3-methylthio-1,2,5-thiadiazol-4-yl)-1-azabicyclo [3.2.1]octane oxalate from endo-6-(3-chloro-1,2,5-thiadiazol-4-yl)-1-azabicyclo[3.2.1]octane and methyliodide. (Compound 85). M.p. 150°–151° C.

Endo-6-(3-isopentylthio-1,2,5-thiadiazol-4-yl)-1-azabicyclo [3.2.1]octane oxalate from endo-6-(3-chloro-1,2,5-thiadiazol-4-yl)-1-azabicyclo[3.2.1]octane and 1-bromo-3-methylbutane. (Compound 86). M.p. 118°–120° C.

Endo-6-(3-isohexylthio-1,2,5-thiadiazol-4-yl)-1-azabicyclo [3.2.1]octane oxalate from endo-6-(3-chloro-1,2,5-thiadiazol-4-yl)-1-azabicyclo[3.2.1]octane and 1-bromo-4-methylpentane. (Compound 87). M.p. 110°–112° C.

Endo-6-(3-benzylthio-1,2,5-thiadiazol-4-yl)-1-azabicyclo [3.2.1]octane oxalate from endo-6-(3-chloro-1,2,5-thiadiazol-4-yl)-1-azabicyclo[3.2.1]octane and benzylchloride. (Compound 88). M.p. 110°–112° C.

Endo-6-(3-cyanomethylthio-1,2,5-thiadiazol-4-yl)-1-azabicyclo[3.2.1]octane oxalate from endo-6-(3-chloro-1, 2,5-thiadiazol-4-yl)-1-azabicyclo[3.2.1]octane and chloroacetonitrile. (Compound 89). M.p. 158°–59° C.

Endo-6-(3-(2-cyanoethylthio)-1,2,5-thiadiazol-4-yl)-1-azabicyclo[3.2.1]octane oxalate from endo-6-(3-chloro-1, 2,5-thiadiazol-4-yl)-1-azabicyclo[3.2.1]octane and 1-bromo-2-cyanoethane. (Compound 90). M.p. 160°–161° C.

Endo-6-(3-(3-cyanopropylthio)-1,2,5-thiadiazol-4-yl)-1-azabicyclo[3.2.1]octane oxalate from endo-6-(3-chloro-1, 2,5-thiadiazol-4-yl)-1-azabicyclo[3.2.1]octane and 1-bromo-3-cyanopropane. (Compound 91). M.p. 119°–120° C.

Endo-6-(3-(4-cyanobutylthio)-1,2,5-thiadiazol-4-yl)-1-azabicyclo[3.2.1]octane oxalate from endo-6-(3-chloro-1, 2,5-thiadiazol-4-yl)-1-azabicyclo[3.2.1]octane and 1-bromo-4-cyanobutane. (Compound 92). M.p. 150°–151° C.

Endo-6-(3-(2-cyanobenzylthio)-1,2,5-thiadiazol-4-yl)-1-azabicyclo[3.2.1]octane oxalate (Compound 227) M.p. 210°–211° C. from endo-6-(3-chloro-1,2,5-thiadiazol-4-yl)-1-azabicyclo[3.2.1]octane and 2-cyanobenzylbromide.

EXAMPLE 44

4-Chloro-3-(3-butoxy-1,2,5-thiadiazol-4-yl)-1-azabicyclo[3.3.1]non-3-ene oxalate To a solution of sodium (0.23 g, 10 mmol) in n-butanol (10 ml) was added 4-chloro-3-(3-chloro-1,2,5-thiadiazol-4-yl)-1-azabicyclo[3.3.1]non-3-ene (Compound 61) (0.274 g, 1 mmol). The reaction mixture was heated at 60° C. for 4 h. Water (100 ml) was added and the water phase extracted with ether (3×50 ml). The combined ether extracts were dried over magnesium sulfate and evaporated. The residue was crystallized from acetone/ether to give the title compound in 200 mg yield. (Compound 93). M.p. 104°–107° C.

EXAMPLE 45

4-Chloro-3-(3-hexyloxy-1,2,5-thiadiazol-4-yl)-1-azabicyclo[3.3.1]non-3-ene hydrochloride The compound was made as described in example 44 by reacting 4-chloro-3-(3-chloro-1,2,5-thiadiazol-4-yl)-1-azabicyclo[3.3.1]non-3-ene with 1-hexanol. The free base was crystallized as the hydrochloride from ether. (Compound 94). M.p. 100°–101° C.

EXAMPLE 46

3-(3-Butoxy-1,2,5-thiadiazol-4-yl)-1-azabicyclo[3.3.1]non-3-ene oxalate

To a solution of 4-chloro-3-(3-butoxy-1,2,5-thiadiazol-4-yl)-1-azabicyclo[3.3.1]non-3-ene (0.63 g, 2.0 mmol) in abs. ethanol (20 ml), triethyl amine (3 ml) and formic acid (1 ml) were added. The reaction mixture was heated to 80° C. under nitrogen. At this temperature palladium on carbon (0.5 g, 5%) was added in one portion. After 15 min. another portion of palladium on carbon (0.25 g, 5%) was added. The last addition of palladium on carbon was repeated twice. After cooling, the reaction mixture was filtered and evaporated. The residue was dissolved in water basified with potassium carbonate and extracted with ether (3×75 ml). The ether extracts were dried and evaporated. The crude compound was purified by column chromatography (eluent: $CH_2Cl_2$/MeOH (9:1)), yielding 80 mg of free base. The title compound was crystallized with oxalic acid from acetone/ether in 80 mg yield. (Compound 95). M.p. 150°–151° C.

EXAMPLE 47

The following compounds were prepared in exactly the same manner as described in example 46.

3-(3-Methoxy-1,2,5-thiadiazol-4-yl)-1-azabicyclo[3.3.1]non-3-ene oxalate from 4-chloro-3-(3-methoxy-1,2,5-thiadiazol-4-yl)-1-azabicyclo[3.3.1]non-3-ene. (Compound 96). M.p. 200°–201° C.

3-(3-Propoxy-1,2,5-thiadiazol-4-yl)-1-azabicyclo[3.3.1]non-3-ene oxalate from 4-chloro-3-(3-propoxy-1,2,5-thiadiazol-4-yl)-1-azabicyclo[3.3.1]non-3-ene. (Compound 97). M.p. 166°–167° C.

3-(3-Hexyloxy-1,2,5-thiadiazol-4-yl)-1-azabicyclo[3.3.1]non-3-ene oxalate from 4-chloro-3-(3-hexyloxy-1,2,5-thiadiazol-4-yl)-1-azabicyclo[3.3.1]non-3-ene. (Compound 98). M.p. 100°–101° C.

EXAMPLE 48

3-(3-Isopentylthio-1,2,5-thiadiazol-4-yl)-1-azabicyclo[2.2.2]octane fumarate

A solution of 3-(3-chloro-1,2,5-thiadiazol-4-yl)-1-azabicyclo[2.2.2]octane (Compound 8) (420 mg, 1.83 mmol), sodiumhydrogen sulfide monohydrate (245 mg, 3.70 mmol) and potassium carbonate (780 mg, 5.64 mmol) in DMF (20 ml) was stirred at room temperature for 2 h. A solution of 1-bromo-3-methylbutane (420 mg, 2.75 mmol) in DMF (5 ml) was added, and the reaction mixture was stirred at room temperature for 3 h. Water (20 ml) was added and the mixture was extracted with ethyl acetate (3×100 ml). The combined extract was washed with brine, dried ($MgSO_4$), filtered and evaporated. The residue was purified by column chromatography (eluent: $CH_2Cl_2$:MeOH:$NH_4OH$ (8:2:0.5%)) to give the free base of the desired product in 400 mg yield. Crystallization of the residue with fumaric acid from isopropanol/ether gave the title compound in 370 mg yield. (Compound 99). M.p. 130°–132° C.

The following compounds were made as described above using the indicated alkylhalogenide instead of 1-bromo-3-methylbutane:

3-(3-(1-Methylpropylthio)-1,2,5-thiadiazol-4-yl)-1-azabicyclo[2.2.2]octane fumarate (Compound 100), using 2-bromobutane.

3-(3-Isobutylthio-1,2,5-thiadiazol-4-yl)-1-azabicyclo[2.2.2]octane fumarate (Compound 101), using 1-bromo-2-methylpropane.

3-(3-(2-Phenoxyethylthio)-1,2,5-thiadiazol-4-yl)-1-azabicyclo[2.2.2]octane fumarate (Compound 102), using β-bromophenetole. M.p. 135°–137° C.

3-(3-Cyanomethylthio-1,2,5-thiadiazol-4-yl)-1-azabicyclo[2.2.2]octane oxalate (Compound 103), using chloroacetonitrile. M.p. 188°–189° C.

3-(3-(3-(2-Thienyl)propylthio)-1,2,5-thiadiazol-4-yl)-1-azabicyclo[2.2.2]octane fumarate (Compound 104), using 1-chloro-3-(2-thienyl)propane. M.p. 134°–136° C.

3-(3-(4-Chlorobutylthio)-1,2,5-thiadiazol-4-yl)-1-azabicyclo[2.2.2]octane (Compound 105), using 1-bromo-4-chlorobutane.

3-(3-Methylthio-1,2,5-thiadiazol-4-yl)-1-azabicyclo[2.2.2]octane oxalate (Compound 131) using bromomethane. M.p. 185°–187° C.

3-(3-(N-(2-Ethylthio)phthalimide)-1,2,5-thiadiazol-4-yl)-1-azabicyclo[2.2.2]octane oxalate (Compound 135) using N-(2-bromoethyl)phthalimide. M.p. 160°–161° C.

3-(3-(2-Methoxyethylthio)-1,2,5-thiadiazol-4-yl)-1-azabicyclo[2.2.2]octane oxalate (Compound 136) using 2-methoxyethylbromide. M.p. 124°–125° C.

3-(3-(2-(1,3-Dioxolan-2-yl)ethylthio)-1,2,5-thiadiazol-4-yl)-1-azabicyclo[2.2.2]octane oxalate (Compound 137) using 2-(1,3-dioxolan-2-yl)ethylbromide. M.p. 151°–153° C.

3-(3-(4-Pyridylmethylthio)-1,2,5-thiadiazol-4-yl)-1-azabicyclo[2.2.2]octane oxalate (Compound 138) using 4-(chloromethyl)pyridine. M.p. 155°–157° C.

3-(3-Cyclopropylmethylthio-1,2,5-thiadiazol-4-yl)-1-azabicyclo[2.2.2]octane oxalate (Compound 139) using cyclopropylmethylbromide. M.p. 217°–218° C.

3-(4-Fluorobenzylthio-1,2,5-thiadiazol-4-yl)-1-azabicyclo[2.2.2]octane oxalate (Compound 140) using 4-fluorobenzylbromide.

3-(3-(2-Hydroxybutylthio)-1,2,5-thiadiazol-4-yl)-1-azabicyclo[2.2.2]octane oxalate (Compound 214) M.p. 180°–182° C., from 1-bromo-2-hydroxybutane.

3-(3-(2-Butanonylthio)-1,2,5-thiadiazol-4-yl)-1-azabicyclo[2.2.2]octane oxalate (Compound 215) M.p. 197°–198° C., from 1-bromo-2-butanone.

3-(3-(3-Phenoxybenzyloxy)-1,2,5-thiadiazol-4-yl)-1-azabicyclo[2.2.2]octane oxalate (Compound 216) M.p. 117°–120° C., from 1-hydroxymethyl-3-phenoxybenzene.

3-(3-(4-Carboxybutylthio)-1,2,5-thiadiazol-4-yl)-1-azabicyclo[2.2.2]octane hydrochloride (Compound 217) M.p. 122°–124° C., from 1-bromo-4-carboxybutane.

3-(3-Hydroxybutylthio)-1,2,5-thiadiazol-4-yl)-1-azabicyclo[2.2.2]octane oxalate (Compound 218) M.p. 140°–141° C., from 1-bromo-3-hydroxybutane.

3-(3-(4-Hydroxybutylthio)-1,2,5-thiadiazol-4-yl)-1-azabicyclo[2.2.2]octane oxalate (Compound 219) M.p. 160°–161° C., from 1-bromo-4-hydroxybutane.

EXAMPLE 49

3-(3-(1-Methyltetrazol-5-ylthio)butylthio-1,2,5-thiadiazol-4-yl)-1-azabicyclo[2.2.2]octane oxalate A solution of 3-(3-(4-chlorobutylthio)-1,2,5-thiadiazol-4-yl)-1-azabicyclo[2.2.2]octane (Compound 105) (3.0 g, 9.5 mmol), potassium carbonate (10 g, 72 mmol) and 1-methyl-5-mercaptotetrazole (5.0 g, 43 mmol) in DMF (50 ml) was stirred at room temperature for 3 days. 1N hydrochloric acid was added to the reaction and the mixture was extracted with ether. The ether phase was discharged. The reaction mixture was made basic with 4N sodium hydroxide and then extracted with ether (3×150 ml). The combined ether phases were dried (MgSO$_4$) and evaporated. The residue was crystallized with oxalic acid from acetone to give the title compound in 420 mg yield. (Compound 106). M.p. 78°–80° C.

The following compounds were made as described above using the indicated mercapto derivative instead of 1-methyl-5-mercaptotetrazole:

3-(3-(2-Methyl-1,3,4-thiadiazol-5-ylthio)butylthio-1,2,5-thiadiazol-4-yl)-1-azabicyclo[2.2.2]octane oxalate (Compound 107), using 2-mercapto-5-methyl-1,3,4-thiadiazole. M.p. 104°–105° C.

3-(3-(4-(2-Benzothiazolyl)thio)butylthio-1,2,5-thiadiazol-4-yl)-1-azabicyclo[2.2.2]octane oxalate (Compound 108), using 2-mercaptobenzothiazole. M.p. 51°–53° C.

EXAMPLE 50

3-(3-(4-Ethylbenzyloxy)-1,2,5-thiadiazol-4-yl)-1-azabicyclo[2.2.2]octane oxalate To a solution of 4-ethylbenzyl alcohol (1.63 g, 12 mmol) in dry THF (20 ml) was added sodium hydride (50% dispersion in mineral oil) (50 mg, 12 mmol) at 0° C. The reaction mixture was stirred for 1 h, then a solution of 3-(3-chloro-1,2,5-thiadiazol-4-yl)-1-azabicyclo[2.2.2] octane (920 mg, 4 mmol) in THF was added dropwise. The reaction mixture was stirred for 3 h. 1N hydrochloric acid was added to the reaction mixture and extracted with ether. The ether phase was discharged. The reaction mixture was made basic with 4N sodium hydroxide and extracted with ether (3×200 ml). The combined ether phases were dried and evaporated. The residue was purified by column chromatography (eluent: CH$_2$Cl$_2$:MeOH:NH$_4$OH (8:2:0.5%)). Crystallization with oxalic acid from acetone gave the title compound in 180 mg yield. (Compound 109). M.p. 100°–102° C.

EXAMPLE 51

The following compound was made as described in example 50 using 3-(2-thienyl)-1-propanol instead of 4-ethylbenzyl alcohol:

3-(3-(3-(2-Thienyl)propoxy)-1,2,5-thiadiazol-4-yl)-1-azabicyclo[2.2.2]octane fumarate. (Compound 110). M.p. 117°–121° C.

EXAMPLE 52

(5S,6S)-6-(3-butylthio-1,2,5-thiadiazol-4-yl)-1-azabicyclo[3.2.1]octane (+)L-tartrate To a solution of (±)exo 6-(3-butylthio-1,2,5-thiadiazol-4-yl)-1-azabicyclo[3.2.1]octane (Compound 30) (28.3 g, 0.1 mol) in a 1:1 mixture of ethanol and ethyl acetate (2.165 l, 50 ml/g) (+)L-tartaric acid (15.0 g, 0.1 mol) was added, and the mixture heated until a clear solution was obtained. After cooling at 4° C. overnight, the precipitated crystals were filtered giving 19.5 g of crude material enriched with (−)exo 6-(3-butylthio-1,2,5-thiadiazol-4-yl)-1-azabicyclo[3.2.1] octane (+)L-tartrate. The mother liquor was evaporated at reduced pressure giving 23.8 g of crude material enriched with (+)exo 6-(3-butylthio-1,2,5-thiadiazol-4-yl)-1-azabicyclo[3.2.1]octane (+)L-tartrate. This material was dissolved in a 1:1 mixture of ethanol/ethyl acetate (1.19 l, 50 ml/g) and heated at reflux. After cooling at 4° C. overnight the precipitated crystals were filtered off. The mother liquor was evaporated and recrystallized from a ethanol/ethyl acetate mixture (50 ml/g). The title compound finally crystallized from the ethanol/ethyl acetate solvent mixture (50 ml/g) in 4.97 g yield. (Compound 111). M.p. 128°–129° C. $[\alpha]_D$=+28.9° (oxalate salt, MeOH). $[\alpha]_D$=+3.71° (free base, MeOH).

EXAMPLE 53

(5R,6R)-6-(3-butylthio-1,2,5-thiadiazol-4-yl)-1-azabicyclo[3.2.1]octane (−)D-tartrate This compound was made in exactly the same manner as described in example 52 using (−)D-tartaric acid (Compound 112). M.p. 128°–130° C. $[\alpha]_D$=−27.5° (oxalate salt, MeOH). $[\alpha]_D$=+3.75° (free base, MeOH).

EXAMPLE 54

(5R,6R)-6-(3-propylthio-1,2,5-thiadiazol-4-yl)-1-azabicyclo[3.2.1]octane (+)L-tartrate To a solution of (±)-exo-6-(3-propylthio-1,2,5-thiadiazol-4-yl)-1-azabicyclo[3.2.1]octane (Compound 58) (4.50 g, 17.6 mmol) in water/ethanol (20:80, 180 ml) was added (+)L-tartaric acid (2.64 g, 17.6 mmol). Ether (90 ml) was added and the mixture was cooled at 4° C. overnight. The precipitated crystals were collected by filtration. Recrystallization twice from ethanol/water/ether (10:40:50) gave the title compound in 1.5 g yield. (Compound 113). M.p. 163°–165° C. $[\alpha]_D$=+4.4° (free base, MeOH).

EXAMPLE 55

(5S,6S)-6-(3-propylthio-1,2,5-thiadiazol-4-yl)-1-azabicyclo[3.2.1]octane (−)D-tartrate This compound was made in exactly the same manner as described in example 54 using (−)D-tartaric acid. (Compound 114). M.p. 164°–165° C. $[\alpha]_D$=−4.2° (free base, MeOH).

EXAMPLE 56

Exo-6-(3-butylsulfonyl-1,2,5-thiadiazol-4-yl)-1-azabicyclo[3.2.1]octane oxalate

An acidic solution of exo 6-(3-butylthio-1,2,5-thiadiazol-4-yl)-1-azabicyclo[3.2.1]octane (Compound 30) (2.5 g, 0.0088 mol) in H$_2$O (20 ml+9 ml 1N HCl) was cooled in an ice-water bath as oxone (8 g, 0.13 mol) in H$_2$O (40 ml) was added dropwise. Cooling was removed and after stirring overnight the reaction was again cooled and the pH adjusted to 9. The mixture was extracted with CHCl$_3$ (3×30 ml), the extracts dried, and the solvent evaporated. The residue was suspended in EtOAc (100 ml) and extracted with saturated aqueous K$_2$CO$_3$ (15 ml), brine, the solvent dried and evaporated to give a yellow oil (2.6 g). The oxalate salt crystallized from EtOAc. M.p. 107°–108° C. (Compound 115). Analysis C$_{13}$H$_{21}$N$_3$O$_2$S$_2$—C$_2$H$_2$O$_4$, C,H,N; Theory C, 44.43; H, 5.72; N, 10.36 Found C, 44.67; H, 5.70; N, 10.38.

Exo-6-(3-(2,2,3,3,4,4,4-heptafluorobutyloxy)-1,2,5-thiadiazol-4-yl)-1-azabicyclo[3.2.1]octane oxalate A suspension of NaH (0.11 g 60% NaH in oil, 0.0028 mol) in THF (15 ml) was cooled to 11° C. as 2,2,3,3,4,4,4- heptafluorobutanol (0.56 g, 0.0074 mol) was added dropwise. After gas evolution ceased, a solution of the free base of (Compound 115) (0.8 g, 0.00254 mol) in THF (25 ml) was added and the reaction warmed to 35°–45° C. for 1.25 h subsequently stirred at ambient overnight and then heated to reflux for 4 h. Another solution of sodium heptafluorobutoxide (0.0028 mol) prepared as above was added and the solution was heated to reflux 1 h. The reaction was treated with $H_2O$ (10 ml), diluted with ether, and extracted with 1N HCl (2×10 ml). The acid extracts were made basic and extracted with EtOAc (3×25 ml). The organic extracts were dried, solvent evaporated and residue purified by radial chromatography (2.5% EtOH-0.25% $NH_4OH$—$CHCl_3$) to give a yellow oil (0.48 g). The oxalate salt crystallized from EtOAc to give a white solid. (Compound 116). M.p. 115°–116° C.

Analysis $C_{13}H_{14}F_7N_3OS$—$C_2H_2O_4$, C,H,N; Theory C, 37.27; H, 3.34; N, 8.69; Found C, 37.55; H, 3.49; N, 8.80.

The following compounds were made in the same manner as described above using the indicated alcohol instead of 2,2,3,3,4,4,4-heptafluorobutanol:

Exo-6-(3-methoxy-1,2,5-thiadiazol-4-yl)-1-azabicyclo[3.2.1]octane oxalate, (Compound 117) using methanol. M.p. 143°–145° C.

Exo-6-(3-ethoxy-1,2,5-thiadiazol-4-yl)-1-azabicyclo[3.2.1]octane oxalate, (Compound 118) using ethanol. M.p. 90°–92° C.

Exo-6-(3-propoxy-1,2,5-thiadiazol-4-yl)-1-azabicyclo[3.2.1]octane oxalate, (Compound 119) using propanol. M.p. 152°–154° C.

Exo-6-(3-butoxy-1,2,5-thiadiazol-4-yl)-1-azabicyclo[3.2.1]octane oxalate, (Compound 120) using butanol.

Exo-6-(3-pentyloxy-1,2,5-thiadiazol-4-yl)-1-azabicyclo[3.2.1]octane oxalate, (Compound 121) using pentanol. M.p. 109°–110° C.

Exo-6-(3-hexyloxy-1,2,5-thiadiazol-4-yl)-1-azabicyclo[3.2.1]octane oxalate, (Compound 122) using hexanol. M.p. 109°–111° C.

Exo-6-(3-isohexyloxy-1,2,5-thiadiazol-4-yl)-1-azabicyclo[3.2.1]octane dioxalate, (Compound 123) using isohexanol. M.p. 94°–96° C.

Exo-6-(3-(2-butynyloxy)-1,2,5-thiadiazol-4-yl)-1-azabicyclo[3.2.1]octane oxalate, (Compound 124) using 2-butyn-1-ol. M.p. 119°–121° C.

EXAMPLE 57

Exo-6-(3-(3-(2-thienyl)-1-propylthio)-1,2,5-thiadiazol-4-yl)-1-azabicyclo[3.2.1]octane oxalate A solution of 6-(3-chloro-1,2,5-thiadiazol-4-yl)-1-azabicyclo[3.2.1]octane (mixture of exo- and endo-isomers (200 mg, 0.9 mmol)) in DMF (10 ml) was cooled to 5° C. whereupon potassium carbonate (180 mg, 1.3 mmol) and sodium hydrosulfide monohydrate (71 mg, 1.0 mmol) were added to the reaction. Stirred for 1 h then potassium carbonate (120 mg, 0.9 mmol) and a solution of 3-(2-thienyl)-1-chloropropane (154 mg, 1.0 mmol) in DMF (5 ml) were added to the reaction and stirred for 1 h at room temperature. The reaction was quenched with water then extracted with ethyl acetate (3×75 ml). The organic phase was dried over $NaCl/Na_2SO_4$ then evaporated. The residue was purified by radial chromatography eluting with 1% $NH_4OH$/10% EtOH in $CHCl_3$. The exo-isomer was isolated and the oxalate salt made to yield 29 mg of the title compound. (Compound 125). M.p. 157°–160° C.

The following compounds were made in exactly the same manner using the appropriate starting material:

Exo-6-(3-(4-fluorobenzylthio)-1,2,5-thiadiazol-4-yl)-1-azabicyclo[3.2.1]octane oxalate (Compound 141) using 4-fluorobenzylbromide. M.p. 152.5°–153.5° C.

Exo-6-(3-(4-chlorobenzylthio)-1,2,5-thiadiazol-4-yl)-1-azabicyclo[3.2.1]octane oxalate (Compound 142) using 4-Chlorobenzylbromide. M.p. 168°–170° C.

Exo-6-(3-(4-methylbenzylthio)-1,2,5-thiadiazol-4-yl)-1-azabicyclo[3.2.1]octane oxalate (Compound 143) using 4-methylbenzylbromide. M.p. 176.5°–178° C.

Exo-6-(3-(4-trifluoromethoxybenzylthio)-1,2,5-thiadiazol-4-yl)-1-azabicyclo[3.2.1]octane oxalate (Compound 144) using 4-trifluoromethoxybenzylbromide. M.p. 175°–176.5° C.

Exo-6-(3-(4-thiocarbamylbenzylthio)-1,2,5-thiadiazol-4-yl)-1-azabicyclo[3.2.1]octane oxalate (Compound 145) using 4-thiocarbamylbenzylbromide. M.p. 125° C. dec.

Exo-6-(3-(4-methylsulfonylbenzylthio)-1,2,5-thiadiazol-4-yl)-1-azabicyclo[3.2.1]octane oxalate (Compound 146) using 4-methylsulfonylbenzylbromide. M.p. 125° C. dec.

Exo-6-(3-(5,5,5-trifluoropentylthio)-1,2,5-thiadiazol-4-yl)-1-azabicyclo[3.2.1]octane oxalate (Compound 147) using 5,5,5-trifluoropentylbromide. M.p. 125°–127° C.

Exo-6-(3-(3,3,3-trifluoropropylthio)-1,2,5-thiadiazol-4-yl)-1-azabicyclo[3.2.1]octane oxalate (Compound 148) using 3,3,3-trifluoropropylbromide. M.p. 93°–96° C.

Endo-6-(3-(3-(2-thienyl)-1-propylthio)-1,2,5-thiadiazol-4-yl)-1-azabicyclo[3.2.1]octane oxalate The endo-isomer was isolated from the above residue in the same manner as described for the exo-isomer. (Compound 126). M.p. 125°–128° C.

Endo-6-(3-(4,4,4-trifluorobutylthio)-1,2,5-thiadiazol-4-yl)-1-azabicyclo[3.2.1]octane oxalate (Compound 127) was made in the same manner as described above using 4,4,4-trifluoro-1-bromobutane instead of 3-(2-thienyl)-1-chloropropane. M.p. 75°–78° C.

Endo-6-(3-(6,6,6-trifluoro-1-hexylthio)-1,2,5-thiadiazol-4-yl)-1-azabicyclo[3.2.1]octane oxalate (Compound 128) was made as described above using 6,6,6-trifluoro-1-bromohexane instead of 3-(2-thienyl)-1-chloropropane. M.p. 130°–133° C.

Endo-6-(3-(4-trifluoromethoxybenzylthio)-1,2,5-thiadiazol-4-yl)-1-azabicyclo[3.2.1]octane oxalate (Compound 149) using 4-trifluoromethoxybenzylbromide. M.p. 150°–152.5° C.

Endo-6-(3-(4-methylbenzylthio)-1,2,5-thiadiazol-4-yl)-1-azabicyclo[3.2.1]octane oxalate (Compound 150) using 4-methylbenzylbromide. M.p. 158°–161° C.

Endo-6-(3-(4-fluorobenzylthio)-1,2,5-thiadiazol-4-yl)-1-azabicyclo[3.2.1]octane oxalate (Compound 151) using 4-fluorobenzylbromide. M.p. 146°–150° C.

Exo-6-(3-cyclopropylmethylthio-1,2,5-thiadiazol-4-yl)-1-azabicyclo[3.2.1]octane oxalate from cyclopropylmethylbromide. (Compound 175). M.p. 200°–201° C.

Exo-6-(3-(2-(1,3-dioxalane-2-yl)-ethylthio)-1,2,5-thiadiazol-4-yl)-1-azabicyclo[3.2.1]octane oxalate from 1-bromo-2-(dioxalanyl)ethane. (Compound 176). M.p. 147°–149° C.

Exo-6-(3-(4-methoxybenzylthio)-1,2,5-thiadiazol-4-yl)-1-azabicyclo[3.2.1]octane oxalate from 4-methoxybenzylchloride. (Compound 177). M.p. 170°–171° C.

Exo-6-(3-(2-methoxyethylthio)-1,2,5-thiadiazol-4-yl)-1-azabicyclo[3.2.1]octane oxalate from 1-bromo-2-methoxyethane. (Compound 178). M.p. 142°–144° C.

Exo-6-(3-(3-hydroxypropylthio)-1,2,5-thiadiazol-4-yl)-1-azabicyclo[3.2.1]octane oxalate from 1-bromo-3-hydroxypropane. (Compound 179). M.p. 115°–116° C.

Exo-6-(3-(4,4,4-trifluorobutylthio)-1,2,5-thiadiazol-4-yl)-1-azabicyclo[3.2.1]octane oxalate from 4,4,4-trifluoro-1-bromobutane. (Compound 180). M.p. 132°–134° C.

Endo-6-(3-cyclopropylmethylthio-1,2,5-thiadiazol-4-yl)-1-azabicyclo[3.2.1]octane oxalate from cyclopropylmethylbromide. (Compound 181). M.p. 152°–154° C.

Endo-6-(3-(4-methoxybenzylthio)-1,2,5-thiadiazol-4-yl)-1-azabicyclo[3.2.1]octane oxalate from 4-methoxybenzylchloride. (Compound 212). M.p. 155°–158° C.

Endo-6-(3-(2-methoxyethylthio)-1,2,5-thiadiazol-4-yl)-1-azabicyclo[3.2.1]octane oxalate from 1-bromo-2-methoxyethane. (Compound 182). M.p. 108°–112° C.

Endo-6-(3-(4-trifluoromethylbenzylthio)-1,2,5-thiadiazol-4-yl)-1-azabicyclo[3.2.1]octane oxalate from 4-trifluoromethylbenzylchloride. (Compound 183). M.p. 154°–156° C.

5-(3-(4-Cyanobenzylthio)-1,2,5-thiadiazol-4-yl)-1-azabicyclo[3.2.1]octane oxalate from 5-(3-chloro-1,2,5-thiadiazol-4-yl)-1-azabicyclo[3.2.1]octane and 4-cyanobenzylchloride. (Compound 172). M.p. 136°–138° C.

EXAMPLE 58

(5S,6S)-6-(3-butylsulfonyl-1,2,5-thiadiazol-4-yl)-1-azabicyclo[3.2.1]octane oxalate A solution of (5S,6S)-6-(3-butylthio-1,2,5-thiadiazol-4-yl)-1-azabicyclo[3.2.1]octane tartrate (Compound 111) (4.4 g, 10.1 mmol) in water was treated with saturated aqueous $NaHCO_3$ until basic then extracted with ethyl acetate (3×100 ml). The organic phase was dried over $NaCl/Na_2SO_4$ then evaporated. The residue was taken up in 1N $HCl_{(aq)}$ and water (23 ml) and cooled to 0° C. A solution of oxone (9.2 g, 15.0 mmol) in water (45 ml) was added dropwise to the reaction then stirred overnight at room temperature. The pH of the reaction was adjusted to 9 then extracted with chloroform. The organic phase was dried over $NaCl/Na_2SO_4$ then evaporated to yield 3.9 g of free base. Crystallization with oxalic acid gave the title compound. (Compound 129). M.p. 147°–151° C.

The following compounds were made in exactly the same manner using the appropriate starting material:

(5R,6R)-6-(3-propylsulfonyl-1,2,5-thiadiazol-4-yl)-1-azabicyclo[3.2.1]octane oxalate (Compound 152) M.p. 160°–162° C.

(5S,6S)-6-(3-propylsulfonyl-1,2,5-thiadiazol-4-yl)-1-azabicyclo[3.2.1]oxtane oxalate (Compound 153) M.p. 160°–162° C.

Exo-6-(3-propylsulfonyl-1,2,5-thiadiazol-4-yl)-1-azabicyclo[3.2.1]octane oxalate. (Compound 184). M.p. 201°–203° C.

(+)3-(3-Butylsulfonyl-1,2,5-thiadiazol-4-yl)-1-azabicyclo[2.2.2]octane oxalate (Compound 220) M.p. 121°–122° C., from (+)3-(3-butylthio-1,2,5-thiadiazol-4-yl)-1-azabicyclo[2.2.2]octane oxalate.

EXAMPLE 59

(5S,6S)-6-(3-(4,4,4-trifluoro-1-butylthio)-1,2,5-thiadiazol-4-yl)-1-azabicyclo[3.2.1]octane oxalate A solution of (5S,6S)-6-(3-butylsulfonyl-1,2,5-thiadiazol-4-yl)-1-azabicyclo[3.2.1]octane (Compound 129) (1.3 g, 4.1 mmol) in DMF (20 ml) was warmed to 40° C. whereupon $Na_2S.9H_2O$ (1.2 g, 5.0 mmol) was added to the reaction. The reaction was heated to 100° C. for 3 h whereupon 1-bromo-4,4,4-trifluorobutane in DMF (5 ml) was added. Stirred at 100° C. for 1 h then at room temperature overnight. Poured the reaction into water then extracted with ethyl acetate (3×100 ml). The organic phase was dried over $NaCl/Na_2SO_4$ then evaporated. The residue was purified by radial chromatography eluting with 2% $NH_4OH/20\%$ EtOH in $CHCl_3$. The oxalate salt was made to yield 545 mg of the title compound (Compound 130). M.p. 147°–151° C.

In the same manner the following compounds were prepared:

(+)3-(3-(2-Butanonylthio)-1,2,5-thiadiazol-4-yl)-1-azabicyclo[2.2.2]octane oxalate (Compound 221) M.p. 189°–191° C., starting from (+)3-(3-butylsulfonyl-1,2,5-thiadiazol-4-yl)-1-azabicyclo[2.2.2]octane and 1-bromo-2-butanone. (+)3-(3-(2-Hydroxybutylthio-1,2,5-thiadiazol-4-yl)-1-azabicyclo[2.2.2]octane oxalate (Compound 222), starting from (+)3-(3-butylsulfonyl-1,2,5-thiadiazol-4-yl)-1-azabicyclo[2.2.2]octane and 1-bromo-2-hydroxybutane.

EXAMPLE 60

3-(1,2,5-Thiadiazol-3-yl)-1-azabicyclo[2.2.2]octane fumarate

To a solution of 1-butanethiol (2.2 ml, 20 mmol) in THF (50 ml) was added sodium hydride (50% suspension in mineral oil, 960 mg, 20 mmol) at 0° C. The reaction was stirred for 1 h, whereafter a solution of 3-(3-chloro-1,2,5-thiadiazol-4-yl)-1-azabicyclo[2.2.2]octane (830 mg, 3.6 mmol) in THF (25 ml) was added. The reaction mixture was stirred at room temperature for 2 h. Water was added and the mixture extracted with ethyl acetate. The organic phase was dried and evaporated and the residue purified by column chromatography (eluent: $CH_2Cl_2:MeOH:NH_4OH$ (80:20:0.5)). Crystallization with fumaric acid from isopropanol/ether gave the title compound in 70 mg yield (Compound 132). M.p. 177°–179° C.

EXAMPLE 61

(5S)-1-Azabicyclo[3.2.1]octan-6-one (+) camphorsulfonate

To a solution of (±)1-azabicyclo[3.2.1]octan-6-one (124 g, 1 mol) in ethanol (100 ml) was added a solution of (+)camphorsulfonic acid (232 g, 1.0 mol) in 200 ml ethanol. The mixture was heated to 70° C. and slowly cooled over 2 hours to 5° C. The precipitated crystals were collected by filtration and washed with cold ethanol (3×40 ml). The crude compound was crystallized from ethanol (150 ml) giving the title compound in 57.3 g yield. M.p. 267°–268° C. (decomp.). $[\alpha]_D=+48°$ (water).

EXAMPLE 62

(5R)-1-Azabicyclo[3.2.1]octan-6-one (−) camphorsulfonate

This compound was made in exactly the same manner as described in example 1 using (±)1-azabicyclo[3.2.1]octan-6-one and (−)camphorsulfonic acid. M.p. 267°–268° C. (decomp.) $[\alpha]_D=-48°$ (water).

EXAMPLE 63

A. (5S)-Ethyl(1-azabicyclo[3.2.1]octan-6-ylidene)cyanoacetate hydrochloride (5R)-1-Azabicyclo[3.2.1]octan-6-one (−)camphorsulfonate (61.8 g, 135.0 mmol) and triethylamine (20.4 g, 202 mmol) and ethyl cyanoacetate (61.8 g, 547 mmol) were mixed and stirred at room temperature for 6 days. Toluene (120 ml) and water (120 ml) were added to the reaction mixture and the pH was adjusted to 2 with concentrated hydrochloric acid. The phases were separated and the water phase extracted with toluene (30 ml). The combined organic phases were washed with water (20 ml). The combined water phases were adjusted to pH=9.4 with $NH_3$ (25% in water) and extracted with toluene (1×120 ml, 1×60 ml). The combined toluene extracts were evaporated. The residue was dissolved in ethanol (120 ml) and concentrated hydrochloric acid (16 ml) was added. The title compound precipitated in 22 g yield. Upon evaporation of the mother liquor and crystallization from ethanol (40 ml) further 14.6 g of the title compound was isolated.

B. Exo- and Endo-6-chloro-6-(3-chloro-1,2,5-thiadiazol-4-yl)-1-azabicyclo[3.2.1]octane (+)L-tartrate (5S)-Ethyl(1-azabicyclo[3.2.1]octan-6-ylidene) cyanoacetate (220 g, 1 mol) was dissolved in abs. ethanol (500 ml). Palladium on carbon (10 g, 5%) was added and the mixture treated with hydrogen in a Parr shaker at 20 psi for 10 hours. The catalyst was filtered off, and the solution evaporated to a final volume of 400 ml. This solution was added to a solution of sodium (25.3 g, 1.1 mol) in ethanol (200 ml). Isoamylnitrite (183.3 g, 1.56 mol) was added at 0°–5° C. The reaction mixture was warmed to room temperature and stirred at this temperature for 6 hours. The reaction mixture was cooled to 4° C. and left at 4° C. overnight. The reaction mixture was evaporated at reduced pressure, toluene (300 ml) was added and the mixture was again evaporated. The residue was dissolved in DMF (300 ml) and slowly added to a mixture of sulfurmonochloride (466 g, 3.5 mol) in DMF (140 ml) at 0°–5° C. The temperature was slowly raised to 20° C. over 3 hours and the reaction mixture was stirred at room temperature overnight. Water (750 ml) was carefully added. The pH was adjusted to 4 by addition of sodiumhydroxide solution (36% NaOH). The mixture was filtered at 70° C., cooled and basified with sodiumhydroxide. The water phase was extracted with toluene (900 ml+400 ml). The organic phases were evaporated. The residue was dissolved in ethanol (670 ml) and (+)L-tartaric acid (117 g, 0.8 mol) was added. The precipitated crystals were filtered giving the title compound in 270 g yield.

The following compounds were prepared in exactly the same manner:

2-Methyl-6-chloro-6-(3-chloro-1,2,5-thiadiazol-4-yl)-1-azabicyclo[3.2.1]octane starting from 2-methyl-1-azabicyclo[3.2.1]octan-6-one.

8-Methyl-6-chloro-6-(3-chloro-1,2,5-thiadiazol-4-yl)-1-azabicyclo[3.2.1]octane starting from 8-methyl-1-azabicyclo[3.2.1]octan-6-one.

C. (5S,6S)-6-(3-chloro-1,2,5-thiadiazol-4-yl)-1-azabicyclo[3.2.1]octane and (5S,6R)-6-(3-chloro-1,2,5-thiadiazol-4-yl)-1-azabicyclo[3.2.1]octane hydrochloride 6-Chloro-6-(3-chloro-1,2,5-thiadiazol-4-yl)-1-azabicyclo[3.2.1]octane (121 g, 0.6 mol) dissolved in ethanol (1.5 l) was treated with Raney Nickel (20 ml, 50%) and hydrogen at atmospheric pressure. The catalyst was filtered and the ethanol evaporated at reduced pressure. The residue was recrystallized from ethanol (400 ml) giving the title compound in 115.8 g yield.

The following compounds were made in exactly the same manner:

Exo-2-methyl-6-(3-chloro-1,2,5-thiadiazol-4-yl)-1-azabicyclo[3.2.1]octane (Compound 169) and endo-2-methyl-6-(3-chloro-1,2,5-thiadiazol-4-yl)-1-azabicyclo[3.2.1]octane (Compound 170) starting from exo/endo-2-methyl-6-chloro-6-(3-chloro-1,2,5-thiadiazol-4-yl)-1-azabicyclo[3.2.1]octane.

Exo-8-methyl-6-(3-chloro-1,2,5-thiadiazol-4-yl)-1-azabicyclo[3.2.1]octane (Compound 171) and endo-8-methyl-6-(3-chloro-1,2,5-thiadiazol-4-yl)-1-azabicyclo[3.2.1]octane (Compound 213) starting from exo/endo-8-methyl-6-chloro-6-(3-chloro-1,2,5-thiadiazol-4-yl)-1-azabicyclo[3.2.1]octane.

D. (5S,6S)-6-(3-butylthio-1,2,5-thiadiazol-4-yl)-1-azabicyclo[3.2.1]octane (+)L-tartrate Starting from a mixture of (5S,6S)- and (5S,6R)-6-(3-chloro-1,2,5-thiadiazol-4-yl)-1-azabicyclo[3.2.1]octane described in example 63C, the chlorine was substituted with butylthio as described in example 14. A 1:9 mixture of (5S,6S)- and (5S,6R)-6-(3-butylthio-1,2,5-thiadiazol-4-yl)-1-azabicyclo[3.2.1]octane (10 g, 35 mmol) was dissolved in toluene (40 ml) and treated with potassium tertbutoxide (0.5 g) at reflux for 1 hour. The toluene solution was washed with water (15 ml) dried and evaporated. The residue crystallized with (+)L-tartaric acid giving the optical pure title compound in 12.5 g yield. (Compound 111). M.p. 128°–129° C.

EXAMPLE 64

Using the (5S,6S), (5R,6R), (5S,6R) and (5R,6S) enantiomers of 6-(3-chloro-1,2,5-thiadiazol-4-yl)-1-azabicyclo[3.2.1]octane (examples 61, 62 and 63) obtained from resolved (5S)-1-azabicyclo[3.2.1]octan-6-one (example 61) or (5R)-1-azabicyclo[3.2.1]octan-6-one (example 62) the following compounds were synthesized using the appropriate alkylhalogenide and separating exo- and endo compounds by column chromatography:

(5R,6R)-6-(3-(4-cyanobenzylthio)-1,2,5-thiadiazol-4-yl)-1-azabicyclo[3.2.1]octane oxalate (Compound 154) using 4-cyanobenzylbromide. M.p. 196°–197° C.

(5S, 6S)-6-(3-(4-cyanobenzylthio)-1,2,5-thiadiazol-4-yl)-1-azabicyclo[3.2.1 ]octane oxalate (Compound 155) using 4-cyanobenzylbromide. M.p. 195°–196° C.

(5S,6R)-6-(3-propylthio-1,2,5-thiadiazol-4-yl)-1-azabicyclo[3.2.1]octane (+)L-tartrate (Compound 156) using propylbromide.

(5R,6R)-6-(3-isohexylthio-1,2,5-thiadiazol-4-yl)-1-azabicyclo[3.2.1]octane (+)L-tartrate (Compound 157) using isohexylbromide. M.p. 152°–153° C.

(5S,6S)-6-(3-isohexylthio-1,2,5-thiadiazol-4-yl)-1-azabicyclo[3.2.1]octane oxalate (Compound 158) using isohexylbromide. M.p. 118°–122° C.

(5R,6S)-6-(3-isohexylthio-1,2,5-thiadiazol-4-yl)-1-azabicyclo[3.2.1]octane (+)L-tartrate (Compound 159) using isohexylbromide. M.p. 102°–103° C.

(5S,6R)-6-(3-(4,4,4-trifluorobutylthio)-1,2,5-thiadiazol-4-yl)-1-azabicyclo[3.2.1]octane (−)D-tartrate (Compound 160) using 4,4,4-trifluorobutylbromide. M.p. 94°–96° C.

(5R,6S)-6-(3-(4,4,4-trifluorobutylthio)-1,2,5-thiadiazol-4-yl)-1-azabicyclo[3.2.1]octane (+)L-tartrate (Compound 161) using 4,4,4-trifluorobutylbromide. M.p. 94°–96° C.

(5S,6R)-6-(3-(4-cyanobenzylthio)-1,2,5-thiadiazol-4-yl)-1-azabicyclo[3.2.1]octane oxalate (Compound 162) using 4-cyanobenzylbromide. M.p. 167°–172° C.

(5R,6S)-6-(3-(4-cyanobenzylthio)-1,2,5-thiadiazol-4-yl)-1-azabicyclo[3.2.1]octane oxalate (Compound 163) using 4-cyanobenzylbromide. M.p. 168°–172° C.

(5R,6S)-6-(3-propylthio-1,2,5-thiadiazol-4-yl)-1-azabicyclo[3.2.1]octane oxalate (Compound 164) using propylbromide. M.p. 64°–65° C.

(5R,6R)-6-(3-(3,3,3-trifluoropropylthio)-1,2,5-thiadiazol-4-yl)-1-azabicyclo[3.2.1]octane hydrochloride (Compound 165) using 3,3,3-trifluoropropylbromide. M.p. 199°–202° C.

(5R,6R)-6-(3-(3-(2-thionyl)propylthio)-1,2,5-thiadiazol-4-yl)-1-azabicyclo[3.2.1]octane oxalate (Compound 166) using 3-(2-thienyl)propylchloride. M.p. 135°–139° C.

(5R,6R)-6-(3-(4,4,4-trifluorobutylthio)-1,2,5-thiadiazol-4-yl)-1-azabicyclo[3.2.1]octane oxalate (Compound 167) using 4,4,4-trifluorobutylbromide. M.p. 153°–154° C.

(5R,6S)-6-(3-(3,3,3-trifluoropropylthio)-1,2,5-thiadiazol-4-yl)-1-azabicyclo[3.2.1]octane hydrochloride (Compound 168) using 3,3,3-trifluoropropylbromide. M.p. 170°–174° C.

(+)-Exo-6-(3-methylthio-1,2,5-thiadiazol-4-yl)-1-azabicyclo[3.2.1]octane oxalate. (Compound 185). M.p. 144°–145° C.

(+)-Exo-6-(3-ethylthio-1,2,5-thiadiazol-4-yl)-1-azabicyclo[3.2.1]octane oxalate. (Compound 186). M.p. 120°–124° C.

(+)-Exo-6-(3-pentylthio-1,2,5-thiadiazol-4-yl)-1-azabicyclo[3.2.1]octane oxalate. (Compound 187). M.p. 128°–129° C.

(+)-Exo-6-(3-hexylthio-1,2,5-thiadiazol-4-yl)-1-azabicyclo[3.2.1]octane oxalate. (Compound 188). M.p. 149°–150° C.

(−)-Exo-6-(3-methylthio-1,2,5-thiadiazol-4-yl)-1-azabicyclo[3.2.1]octane oxalate. (Compound 189). M.p. 144°–145° C.

(−)-Exo-6-(3-ethylthio-1,2,5-thiadiazol-4-yl)-1-azabicyclo[3.2.1]octane oxalate. (Compound 190). M.p. 120°–123° C.

(−)-Exo-6-(3-pentylthio-1,2,5-thiadiazol-4-yl)-1-azabicyclo[3.2.1]octane oxalate. (Compound 191). M.p. 132°–1340C.

(−)-Exo-6-(3-hexylthio-1,2,5-thiadiazol-4-yl)-1-azabicyclo[3.2.1]octane oxalate. (Compound 192). M.p. 149°–150° C.

(+)-Endo-6-(3-methylthio-1,2,5-thiadiazol-4-yl)-1-azabicyclo[3.2.1]octane oxalate. (Compound 193). M.p. 138°–139° C.

(+)-Endo-6-(3-ethylthio-1,2,5-thiadiazol-4-yl)-1-azabicyclo[3.2.1]octane oxalate. (Compound 194). M.p. 87°–89° C.

(+)-Endo-6-(3-pentylthio-1,2,5-thiadiazol-4-yl)-1-azabicyclo[3.2.1]octane oxalate. (Compound 195). M.p. 65°–70° C.

(+)-Endo-6-(3-hexylthio-1,2,5-thiadiazol-4-yl)-1-azabicyclo[3.2.1]octane oxalate. (Compound 196). M.p. 89°–90° C.

(−)-Endo-6-(3-methylthio-1,2,5-thiadiazol-4-yl)-1-azabicyclo[3.2.1]octane oxalate. (Compound 197). M.p. 137°–140° C.

(−)-Endo-6-(3-ethylthio-1,2,5-thiadiazol-4-yl)-1-azabicyclo[3.2.1]octane oxalate. (Compound 198). M.p. 107°–110° C.

(−)-Endo-6-(3-pentylthio-1,2,5-thiadiazol-4-yl)-1-azabicyclo[3.2.1]octane oxalate. (Compound 199). M.p. 85°–90° C.

(−)-Endo-6-(3-hexylthio-1,2,5-thiadiazol-4-yl)-1-azabicyclo[3.2.1]octane oxalate. (Compound 200). M.p. 132°–134° C.

(+)-Exo-6-(3-(4-trifluoromethylbenzylthio)-1,2,5-thiadiazol-4-yl)-1-azabicyclo[3.2.1]octane oxalate from 4-trifluoromethylbenzylchloride. (Compound 201). M.p. 172°–174° C.

(+)-Exo-6-(3-(4-nitrobenzylthio)-1,2,5-thiadiazol-4-yl)-1-azabicyclo[3.2.1]octane oxalate from 4-nitrobenzylchloride. (Compound 202). M.p. 173°–174° C.

(+)-Exo-6-(3-(2-hydroxyethylthio)-1,2,5-thiadiazol-4-yl)-1-azabicyclo[3.2.1]octane oxalate from 2-hydroxy-1-chloroethane. (Compound 203). M.p. 179°–181° C.

(+)-Exo-6-(3-(2-propanonylthio)-1,2,5-thiadiazol-4-yl)-1-azabicyclo[3.2.1]octane oxalate (Compound 228) using 1-bromo-2-propanone. M.p. 151°–154° C.

(+)-Exo-6-(3-(2-hydroxypropylthio)-1,2,5-thiadiazol-4-yl)-1-azabicyclo[3.2.1]octane oxalate (Compound 229) using 1-bromo-2-hydroxypropane. M.p. 179°–180° C.

(+)-Exo-6-(3-(3-phenylpropylthio)-1,2,5-thiadiazol-4-yl)-1-azabicyclo[3.2.1]octane oxalate (Compound 230) using 1-bromo-3-phenylpropane. M.p. 135°–136° C.

(−)-Exo-6-(3-(3-phenylpropylthio)-1,2,5-thiadiazol-4-yl)-1-azabicyclo[3.2.1]octane oxalate (Compound 231) using 1-bromo-3-phenylpropane. M.p. 135°–136° C.

(+)-Endo-6-(3-(3-phenylpropylthio)-1,2,5-thiadiazol-4-yl)-1-azabicyclo[3.2.1]octane oxalate (Compound 232) using 1-bromo-3-phenylpropane. M.p. 110°–113° C.

(−)-Endo-6-(3-(3-phenylpropylthio)-1,2,5-thiadiazol-4-yl)-1-azabicyclo[3.2.1 ]octane oxalate (Compound 233) using 1-bromo-3-phenylpropane. M.p. 100°–106° C.

(+)-Exo-6-(3-(4-fluorophenoxyethylthio)-1,2,5-thiadiazol-4-yl)-1-azabicyclo[3.2.1]octane oxalate (Compound 234) using 1-bromo-2-(4-fluorophenoxy)ethane.

(−)-Exo-6-(3-(4-fluorophenoxyethylthio)-1,2,5-thiadiazol-4-yl)-1-azabicyclo[3.2.1]octane oxalate (Compound 235) using 1-bromo-2-(4-fluorophenoxy)ethane. M.p. 132°–137° C.

(+)-Endo-6-(3-(4-fluorophenoxyethylthio)-1,2,5-thiadiazol-4-yl)-1azabicyclo[3.2.1]octane oxalate (Compound 236) using 1-bromo-2-(4-fluorophenoxy)ethane.

(−)-Endo-6-(3-(4-fluorophenoxyethylthio)-1,2,5-thiadiazol-4-yl)-1-azabicyclo[3.2.1]octane oxalate (Compound 237) using 1-bromo-2-(4-fluorophenoxy)ethane. M.p. 144°–147° C.

In the above examples optical rotation is measured on the free base.

EXAMPLE 65

The following compounds were prepared in exactly the same manner as described in example 64:

Endo-2-methyl-6-(3-propylthio-1,2,5-thiadiazol-4-yl)-1-azabicyclo[3.2.1]octane oxalate from endo-2-methyl-6-(3-chloro-1,2,5-thiadiazol-4-yl)-1-azabicyclo[3.2.1]octane. (Compound 204). M.p. 123°–124° C.

Endo-8-methyl-6-(3-propylthio-1,2,5-thiadiazol-4-yl)-1-azabicyclo[3.2.1]octane oxalate from endo-8-methyl-6-(3-chloro-1,2,5-thiadiazol-4-yl)-1-azabicyclo[3.2.1]octane. (Compound 205). M.p. 172°–175° C.

Exo-2-methyl-6-(3-propylthio-1,2,5-thiadiazol-4-yl)-1-azabicyclo[3.2.1]octane oxalate from exo-2-methyl-6-(3-chloro-1,2,5-thiadiazol-4-yl)-1-azabicyclo[3.2.1]octane. (Compound 206). M.p. 155°–156° C.

Exo-8-methyl-6-(3-propylthio-1,2,5-thiadiazol-4-yl)-1-azabicyclo[3.2.1]octane oxalate from exo-8-methyl-6-(3-chloro-1,2,5-thiadiazol-4-yl)-1-azabicyclo[3.2.1]octane. (Compound 207). M.p. 144°–146° C.

Exo-2-methyl-6-(3-butylthio-1,2,5-thiadiazol-4-yl)-1-azabicyclo[3.2.1]octane oxalate from exo-2-methyl-6-(3-chloro-1,2,5-thiadiazol-4-yl)-1-azabicyclo[3.2.1]octane. (Compound 208). M.p, 160°–164° C.

Exo-8-methyl-6-(3-butylthio-1,2,5-thiadiazol-4-yl)-1-azabicyclo[3.2.1]octane oxalate from exo-8-methyl-6-(3- chloro-1,2,5-thiadiazol-4-yl)-1-azabicyclo[3.2.1]octane. (Compound 209). M.p. 143°–147° C.

Exo-2-methyl-6-(3-hexylthio-1,2,5-thiadiazol-4-yl)-1-azabicyclo[3.2.1]octane oxalate from exo-2-methyl-6-(3-chloro-1,2,5-thiadiazol-4-yl)-1-azabicyclo[3.2.1]octane. (Compound 210). M.p. 128°–131° C.

Exo-8-methyl-6-(3-hexylthio-1,2,5-thiadiazol-4-yl)-1-azabicyclo[3.2.1]octane oxalate from exo-8-methyl-6-(3-chloro-1,2,5-thiadiazol-4-yl)-1-azabicyclo[3.2.1]octane. (Compound 211). M.p. 140°–142° C.

We claim:

1. A method of treating a urinary bladder dysfunction in a subject in need thereof comprising administering to the subject an effective amount of a compound of formula I

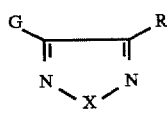

(I)

wherein

X is oxygen or sulphur;

R is hydrogen, amino, halogen, —CHO, —NO$_2$, —R$^4$, —Y, —NHCO—R$^4$, —OR$^4$, —SR$^4$, —SOR$^4$, —SO$_2$R$^4$, C$_{3-10}$-cycloalkyl, C$_{4-10}$-cycloalkenyl, C$_{4-10}$-(cycloalkylalkyl), —Z$^1$—C$_{3-10}$-cycloalkyl, —Z$^1$—C$_{4-10}$-cycloalkenyl, —Z$^1$—C$_{4-10}$-(cycloalkylalkyl), —Z$^1$—C$_{4-10}$-(cycloalkenylalkyl), —Z$^1$—C$_{4-10}$-(methylenecycloalkylalkyl), —NH—R$^4$, —NR$^4$R$^5$, —NH—OR$^4$, —CH=NOR$^4$, or an aromatic ring selected from the group consisting of phenyl, benzyloxycarbonyl, phenoxy, benzoyl, tetrahydronaphthyl, naphtyl, and indenyl, wherein each aromatic ring is optionally substituted with halogen, —NO$_2$, —CN, C$_{1-4}$-alkyl, C$_{1-4}$-alkoxy, —OCF$_3$, —CONH$_2$, —CSNH$_2$, phenoxy or phenyl; or R is —Z$^1$—R$^6$—Z$^2$—R$^5$, —Z$^1$—R$^6$—Z$^2$—R$^7$—Z$^3$—R$^5$, —Z$^1$—CO—R$^5$, —Z$^1$—R$^6$—CO—R$^5$, —Z$^1$—R$^6$—CO$_2$—R$^5$, —Z$^1$—R$^6$—O$_2$C—R$^5$, —Z$^1$—R$^6$—COHN—R$^5$, —Z$^1$—R$^6$—NHCO—R$^5$, —Z$^1$—R$^6$—Y, —Z$^1$—R$^6$—Z$^2$—Y, wherein Z$^1$ and Z$^2$ independently are oxygen or sulphur, and R$^4$ and R$^5$ independently are straight or branched C$_{1-15}$-alkyl, straight or branched C$_{2-15}$-alkenyl, straight or branched C$_{2-15}$-alkynyl, each of which is optionally substituted with one or more halogen(s), C$_{1-6}$-alkoxy, —CF$_3$, —CN, —COOH, —OH, —NH$_2$, C$_{1-6}$-alkyl ester, —SH, —NHR$^4$, —NR$^4$R$^5$, or a phenyl or phenoxy group, wherein the phenyl or phenoxy group is optionally substituted with halogen, —NO$_2$, —CN, C$_{1-4}$-alkyl, C$_{1-4}$-alkoxy, —OCF$_3$, —CONH$_2$, —CSNH$_2$, phenyl or phenoxy, and wherein R$^6$ and R$^7$ independently are straight or branched C$_{1-10}$-alkylene, straight or branched C$_{2-10}$-alkenylene, straight or branched C$_{2-10}$-alkynylene, each of which is optionally substituted with one or more halogen(s), —CF$_3$, —CN, —COOH, —OH, —NH$_2$, C$_{1-6}$-alkyl ester, —SH, —NHR$^4$, —NR$^4$R$^5$, phenyl or phenoxy, and Y is a heterocyclic group selected from the group consisting of thienyl, tetrazolyl, thiadiazolyl, benzothiazolyl, phthalimido, pyridyl and 1,3-dioxolanyl wherein the heterocyclic group is optionally substituted at carbon or nitrogen atom(s) with straight or branched C$_{1-6}$-alkyl, phenyl or benzyl, or a carbon atom of the heterocyclic group together with an oxygen atom to form a carbonyl group, or wherein the heterocyclic group is optionally fused with a phenyl group; and G is an azabicyclic ring of formula II

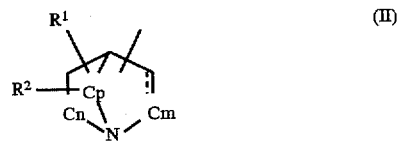

(II)

wherein the thiadiazole or oxadiazole ring is attached to any carbon atom of the azabicyclic ring;

R$^1$ and R$^2$ may be present at any appropriate position of the thiadiazole or oxadiazole ring and independently are hydrogen, straight or branched C$_{1-5}$-alkyl, straight or branched C$_{2-5}$-alkenyl, straight or branched C$_{2-5}$-alkynyl, straight or branched C$_{1-10}$-alkoxy, —OH, halogen, —NH$_2$, carboxy or straight or branched C$_{1-5}$-alkyl substituted with —OH; m and n are 2; p is 1; and ..... is a single or double bond; or a pharmaceutically acceptable salt thereof.

2. The method according to claim 1, wherein X is S.

3. The method according to claim 1, wherein R$^1$ and R$^2$ independently are hydrogen, methyl, methoxy, hydroxy, halogen or amino.

4. The method according to claim 1, wherein R$^1$ and R$^2$ are hydrogen.

5. The method according to claim 4, wherein R$^4$ is straight or branched C$_{1-15}$-alkyl.

6. The method according to claim 4, wherein R$^4$ is branched C$_{4-15}$-alkyl.

7. The method according to claim 4, wherein R$^4$ is straight C$_{3-5}$-alkyl.

8. The method according to claim 1, wherein the compound is selected from the following:

4-Chloro-3-(3-chloro-1,2,5-thiadiazol-4-yl)-1-azabicyclo[3.3.1]non-3-ene;

4-Chloro-3-(3-propyloxy-1,2,5-thiadiazol-4-yl)-1-azabicyclo[3.3.1]non-3-ene;

4-Chloro-3-(3-pentyloxy-1,2,5-thiadiazol-4-yl)-1-azabicyclo[3.3.1]non-3-ene;

4-Chloro-3-(3-methoxy-1,2,5-thiadiazol-4-yl)-1-azabicyclo[3.3.1]non-3-ene;

4-Chloro-3-(1,2,5-thiadiazol-4-yl)-1-azabicyclo[3.3.1]non-3-ene;

4-Chloro-3-(3-butoxy-1,2,5-thiadiazol-4-yl)-1-azabicyclo[3.3.1]non-3-ene;

4-Chloro-3-(3-hexyloxy-1,2,5-thiadiazol-4-yl)-1-azabicyclo[3.3.1]non-3-ene;

3-(3-Butoxy-1,2,5-thiadiazol-4-yl)-1-azabicyclo[3.3.1]non-3-ene;

3-(3-Methoxy-1,2,5-thiadiazol-4-yl)-1-azabicyclo[3.3.1]non-3-ene;

3-(3-Propoxy-1,2,5-thiadiazol-4-yl)-1-azabicyclo[3.3.1]non-3-ene;

3-(3-Hexyloxy-1,2,5-thiadiazol-4-yl)-1-azabicyclo[3.3.1]non-3-ene; or a pharmaceutically acceptable salt thereof.

* * * * *